(12) United States Patent
Anselm et al.

(10) Patent No.: US 8,822,505 B2
(45) Date of Patent: Sep. 2, 2014

(54) AZETIDINE DERIVATIVES

(71) Applicant: Hoffmann-La Roche Inc., Nutley, NJ (US)

(72) Inventors: Lilli Anselm, Binzen (DE); David Banner, Basel (CH); Wolfgang Haap, Loerrach (DE); Bernd Kuhn, Reinach (CH); Thomas Luebbers, Loerrach (DE); Jens-Uwe Peters, Grenzach-Wyhlen (DE); Beat Spinnler, Allschwil (CH)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/760,519

(22) Filed: Feb. 6, 2013

(65) Prior Publication Data
US 2013/0210799 A1    Aug. 15, 2013

(30) Foreign Application Priority Data

Feb. 7, 2012    (EP) .................................... 12154244

(51) Int. Cl.
*C07D 401/14* (2006.01)
*A61K 31/444* (2006.01)

(52) U.S. Cl.
CPC .................................. *C07D 401/14* (2013.01)
USPC ...................... 514/343; 546/278.4

(58) Field of Classification Search
USPC ........................................ 546/278.4; 514/343
See application file for complete search history.

*Primary Examiner* — Bruck Kifle
(74) *Attorney, Agent, or Firm* — Robert C. Hall

(57) ABSTRACT

The invention relates to a compound of formula (I)

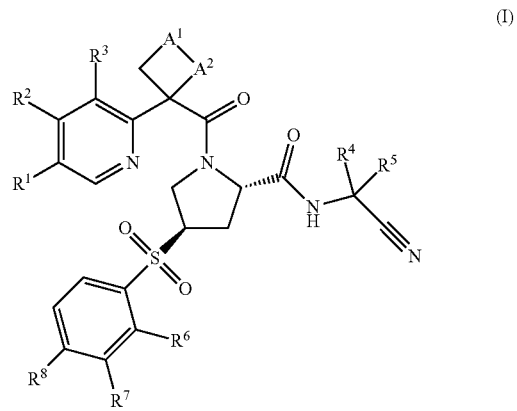

wherein $A^1$, $A^2$ and $R^1$ to $R^8$ are defined as in the description and in the claims. The compound of formula (I) can be used as a medicament.

18 Claims, No Drawings

AZETIDINE DERIVATIVES

CROSS REFERENCE TO RELATED APPLICATIONS

This application claims priority under 35 USC §119 to EP Application No. 12154244.3 filed on Feb. 7, 2012, the disclosure of which is incorporated herein by reference.

FIELD OF THE INVENTION

The present invention relates to organic compounds useful for therapy and/or prophylaxis in a mammal, and in particular to compounds that are preferential inhibitors of the cysteine protease cathepsin, in particular of the cysteine protease cathepsin S or L.

BACKGROUND OF THE INVENTION

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme, D. (2001), 'Papain-like cysteine proteases', Curr Protoc Protein Sci, Chapter 21, Unit 21 2; Roberts, R. (2005), 'Lysosomal cysteine proteases: structure, function and inhibition of cathepsins', Drug News Perspect, 18 (10), 605-14).

Cathepsin S is prominently expressed in antigen presenting cells like macrophages and dendritic cells and smooth muscle cells. (Hsing, L. C. and Rudensky, A. Y. (2005), 'The lysosomal cysteine proteases in MHC class II antigen presentation', Immunol Rev, 207, 229-41; Rudensky, A. and Beers, C. (2006), 'Lysosomal cysteine proteases and antigen presentation', Ernst Schering Res Found Workshop, (56), 81-95). While Cathepsin S is only weakly expressed in normal arterial tissue, strong upregulation is seen in atherosclerotic arteries (Liu, J., et al. (2006), 'Increased serum cathepsin S in patients with atherosclerosis and diabetes', Atherosclerosis, 186 (2), 411-9; Sukhova, G. K., et al. (1998), 'Expression of the elastolytic cathepsins S and K in human atheroma and regulation of their production in smooth muscle cells', J Clin Invest, 102 (3), 576-83).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice a significant reduction of acute plaque rupture events was reported. When chronic renal disease is introduced into CatS/InAPO-E deficient mice a strong reduction of accelerated calcification is seen on top of the anti atherosclerotic activity in arteries and heart valves Aikawa, E., et al. (2009), 'Arterial and aortic valve calcification abolished by elastolytic cathepsin S deficiency in chronic renal disease', Circulation, 119 (13), 1785-94; de Nooijer, R., et al. (2009), 'Leukocyte cathepsin S is a potent regulator of both cell and matrix turnover in advanced atherosclerosis', Arterioscler Thromb Vasc Biol, 29 (2), 188-94; Rodgers, K. J., et al. (2006), 'Destabilizing role of cathepsin S in murine atherosclerotic plaques', Arterioscler Thromb Vasc Biol, 26 (4), 851-6; Sukhova et al. (2003), 'Deficiency of cathepsin S reduces atherosclerosis in LDL receptor-deficient mice', J Clin Invest, 111 (6), 897-906). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly, Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of T cells to the chronic inflammation of the atherosclerotic tissue. Elevated inflammation results in further oxidative and proteolytic tissue damage and subsequently plaque destabilisation (Cheng, X. W., et al. (2004), 'Increased expression of elastolytic cysteine proteases, cathepsins S and K, in the neointima of balloon-injured rat carotid arteries', Am J Pathol, 164 (1), 243-51; Driessen, C., et al. (1999), 'Cathepsin S controls the trafficking and maturation of MHC class II molecules in dendritic cells', J Cell Biol, 147 (4), 775-90; Rudensky, A. and Beers, C. (2006), 'Lysosomal cysteine proteases and antigen presentation', Ernst Schering Res Found Workshop, (56), 81-95).

The anti-inflammatory and anti-elastinolytic properties of a Cat S inhibitor make it also a prominent target for chronic obstructive pulmonary disease (Williams, A. S., et al. (2009), 'Role of cathepsin S in ozone-induced airway hyperresponsiveness and inflammation', Pulm Pharmacol Ther, 22 (1), 27-32). Furthermore due to its extracellular functions in matrix degradation, inhibition of cathepsin S will impact neointima formation and angiogenesis (Burns-Kurtis, C. L., et al. (2004), 'Cathepsin S expression is up-regulated following balloon angioplasty in the hypercholesterolemic rabbit', Cardiovasc Res, 62 (3), 610-20; Cheng, X. W., et al. (2004), 'Increased expression of elastolytic cysteine proteases, cathepsins S and K, in the neointima of balloon-injured rat carotid arteries', Am J Pathol, 164 (1), 243-51; Shi, G. P., et al. (2003), 'Deficiency of the cysteine protease cathepsin S impairs microvessel growth', Circ Res, 92 (5), 493-500; Wang, B., et al. (2006), 'Cathepsin S controls angiogenesis and tumor growth via matrix-derived angiogenic factors', J Biol Chem, 281 (9), 6020-9). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15 (19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

Cathepsin L shows a broader expression profile than cathepsin S and there are also data which suggest a role of cathepsin L in atherosclerosis, e.g. LDLrec & Cat L deficient mice show a reduced atherosclerotic phenotype (Kitamoto, S., et al. (2007), 'Cathepsin L deficiency reduces diet-induced atherosclerosis in low-density lipoprotein receptor-knockout mice', Circulation, 115 (15), 2065-75). In addition, Cat L was suggested to be involved in metabolic syndrome as it controls adipogenesis and peripheral glucose tolerance. In renal disease Cathepsin L is described to regulate podocyte function by proteolytically processing dynamin and thereby proteinuria (Sever, S., et al. (2007), 'Proteolytic processing of dynamin by cytoplasmic cathepsin L is a mechanism for proteinuric kidney disease', J Clin Invest, 117 (8), 2095-104).

Tissue remodelling, extracellular matrix degradation, the generation of active neuropeptides and roles in antigen presentation in thymic epithelial cells are cellular activities described for Cathepsin L (Funkelstein et al. (2008), (a) 'Major role of cathepsin L for producing the peptide hormones ACTH, β-Endorphin, and α-MSH, illustrated by protease gene knockout and expression', Journal of Biological Chemistry, 283 (51), 35652-35659; (b) 'Cathepsin L participates in the production of neuropeptide Y in secretory vesicles, demonstrated by protease gene knockout and expression', Journal of Neurochemistry, 106(1), 384-391; Rudensky and Beers 2006).

SUMMARY OF THE INVENTION

The invention relates in particular to a compound of formula (I)

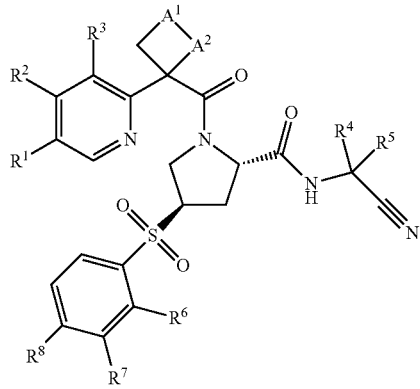

wherein
one of $A^1$ and $A^2$ is —$NR^9$— and the other one is —$CH_2$—;
$R^1$ is halogen;
$R^2$ is hydrogen, halogen, alkyl or haloalkyl;
$R^3$ is hydrogen, halogen, alkyl or haloalkyl;
$R^4$ and $R^5$ are both hydrogen at the same time;
or $R^4$ and $R^5$ together with the carbon atom to which they are attached form cycloalkyl;
$R^6$ is hydrogen, halogen, alkyl, haloalkyl or cycloalkyl;
$R^7$ is hydrogen, halogen, alkyl, haloalkyl or cycloalkyl;
$R^8$ is hydrogen, alkyl, haloalkyl, alkoxy, haloalkoxy, cycloalkyl, alkylpyrdinyl, alkyl-1H-pyrazolyl, phenyl, substituted phenyl, heterocyclyl or substituted heterocyclyl, wherein heterocyclyl is pyridinyl, pyrimidinyl, pyrazinyl, pyridazinyl, pyrrolyl, pyrazolyl, imidazolyl, triazolyl, oxazolyl, isoxazolyl, oxadiazolyl, thiophenyl, thiazolyl, thiadiazolyl, piperidinyl, piperazinyl, pyrrolidinyl or morpholinyl, wherein substituted phenyl is phenyl substituted with one to three substituents independently selected from alkyl, halogen, cycloalkyl, haloalkyl, alkoxy, haloalkoxy, halocycloalkyl and nitrile and wherein substituted heterocyclyl is heterocyclyl substituted with one to three substituents independently selected from alkyl, halogen, cycloalkyl, haloalkyl, alkoxy, haloalkoxy, halocycloalkyl and nitrile; and
$R^9$ is hydrogen, alkyl, haloalkyl, cycloalkyl, acyl or alkoxycarbonyl;
or a pharmaceutically acceptable salt or ester thereof.

The compounds of the invention are preferential inhibitors of the cysteine protease Cathepsin (Cat), in particular Cathepsin S or Cathepsin L and are therefore useful to treat metabolic diseases like diabetes, atherosclerosis, abdominal aortic aneurysm, peripheral arterial disease, cancer, reduction of cardiovascular events in chronic kidney disease, glomerulonephritis, age related macular degeneration, diabetic nephropathy and diabetic retinopathy. In addition, immune mediated diseases like rheumatoid arthritis, crohn's disease, multiple sclerosis, sjorgen syndrome, lupus erythematosus, neuropathic pain, diabetes type I, asthma and allergy and skin related immune disease are suitable diseases to be treated with a cathepsin S inhibitor.

Objects of the present invention are the compounds of formula (I) and their aforementioned salts per se and their use as therapeutically active substances, a process for the manufacture of the said compounds, intermediates, pharmaceutical compositions, medicaments containing the said compounds, their pharmaceutically acceptable salts, the use of the said compounds and salts for the prophylaxis and/or therapy of illnesses, especially in the treatment or prophylaxis of diabetes, atherosclerosis, abdominal aortic aneurysm, peripheral arterial disease, cancer, reduction of cardiovascular events in chronic kidney disease and diabetic nephropathy, and the use of the said compounds and salts for the production of medicaments for the treatment or prophylaxis of diabetes, atherosclerosis, abdominal aortic aneurysm, peripheral arterial disease, cancer, reduction of cardiovascular events in chronic kidney disease and diabetic nephropathy.

DETAILED DESCRIPTION OF THE INVENTION

In the present description the term "alkyl", alone or in combination, signifies a straight-chain or branched-chain alkyl group with 1 to 8 carbon atoms, in particular a straight or branched-chain alkyl group with 1 to 6 carbon atoms and particularly a straight or branched-chain alkyl group with 1 to 4 carbon atoms. Examples of straight-chain and branched C1-C8 alkyl groups are methyl, ethyl, propyl, isopropyl, butyl, isobutyl, tert.-butyl, the isomeric pentyls, the isomeric hexyls, the isomeric heptyls and the isomeric octyls, in particular methyl, ethyl, propyl, isopropyl, isobutyl and tert.-butyl, more particularly methyl and ethyl.

The term "cycloalkyl", alone or in combination, signifies a cycloalkyl ring with 3 to 8 carbon atoms and particularly a cycloalkyl ring with 3 to 6 carbon atoms. Examples of C3-C8 cycloalkyl are cyclopropyl, cyclobutyl, cyclopentyl, cyclohexyl, cycloheptyl and cyclooctyl. Particular cycloalkyl are cyclopropyl, cyclobutyl, cyclopentyl and cyclohexyl. Cyclopropyl is a particular cycloalkyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, in particular methoxy and tert.butoxy.

The term "oxy", alone or in combination, signifies the —O— group.

The term "halogen" or "halo", alone or in combination, signifies fluorine, chlorine, bromine or iodine, in particular fluorine, chlorine or bromine.

The terms "haloalkyl", "halocycloalkyl" and "haloalkoxy", alone or in combination, denote an alkyl group, a cycloalkyl group and an alkoxy group substituted with at least one halogen, in particular substituted with one to five halogens, particularly one to three halogens. Fluoroalkyl is an alkyl group substituted with at least one fluorine atom, particularly substituted with one to five fluorine atoms, more particularly one to three fluorine atoms. Particular haloalkyl are difluoroethyl and trifluoroethyl. Particular haloalkoxy are trifluoroethoxy and trifluoropropyloxy.

The term "carbonyl", alone or in combination, signifies the —C(O)— group.

The term "acyl", alone or in combination, is used to mean the formyl group (—CH(O)).

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, in particular, hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins. The compound of formula (I) can also be present in the form of zwitterions. Particular pharmaceutically acceptable salts of compound of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contains one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates to a compound of formula (I)

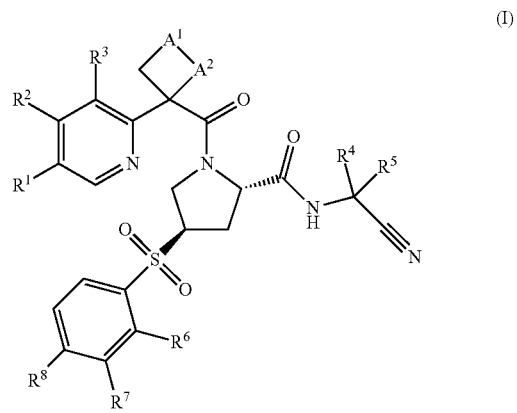

(I)

wherein
one of $A^1$ and $A^2$ is —$NR^9$— and the other one is —$CH_2$—;
$R^1$ is halogen;
$R^2$ is hydrogen, halogen, alkyl or haloalkyl;
$R^3$ is hydrogen, halogen, alkyl or haloalkyl;
$R^4$ and $R^5$ are both hydrogen at the same time;
or $R^4$ and $R^5$ together with the carbon atom to which they are attached form cycloalkyl;
$R^6$ is hydrogen, halogen, alkyl, haloalkyl or cycloalkyl;
$R^7$ is hydrogen, halogen, alkyl, haloalkyl or cycloalkyl;
$R^8$ is hydrogen, alkyl, haloalkyl, alkoxy, haloalkoxy, cycloalkyl, alkylpyrdinyl, alkyl-1H-pyrazolyl, phenyl, substituted phenyl, heterocyclyl or substituted heterocyclyl, wherein heterocyclyl is pyridinyl, pyrimidinyl, pyrazinyl, pyridazinyl, pyrrolyl, pyrazolyl, imidazolyl, triazolyl, oxazolyl, isoxazolyl, oxadiazolyl, thiophenyl, thiazolyl, thiadiazolyl, piperidinyl, piperazinyl, pyrrolidinyl or morpholinyl, wherein substituted phenyl is phenyl substituted with one to three substituents independently selected from alkyl, halogen, cycloalkyl, haloalkyl, alkoxy, haloalkoxy, halocycloalkyl and nitrile and wherein substituted heterocyclyl is heterocyclyl substituted with one to three substituents independently selected from alkyl, halogen, cycloalkyl, haloalkyl, alkoxy, haloalkoxy, halocycloalkyl and nitrile; and
$R^9$ is hydrogen, alkyl, haloalkyl, cycloalkyl, acyl or alkoxycarbonyl;
or a pharmaceutically acceptable salt or ester thereof.

The invention relates in particular to the following:
A compound of formula (I) wherein $A^1$ is —$NR^9$—;
A compound of formula (I) wherein $A^1$ is —$CH_2$—;
A compound of formula (I) wherein $A^2$ is —$NR^9$—;
A compound of formula (I) wherein $A^2$ is —$CH_2$—;
A compound of formula (I) wherein $R^1$ is chloro or bromo;
A compound of formula (I) wherein $R^2$ is hydrogen;
A compound of formula (I) wherein $R^3$ is hydrogen or halogen;
A compound of formula (I) wherein $R^3$ is hydrogen or fluoro;
A compound of formula (I) wherein $R^4$ and $R^5$ together with the carbon atom to which they are attached form cyclopropyl;
A compound of formula (I) wherein $R^6$ is halogen;
A compound of formula (I) wherein $R^6$ is chloro;
A compound of formula (I) wherein $R^7$ is hydrogen;
A compound of formula (I) wherein $R^8$ is hydrogen, halogen, alkoxy, haloalkoxy, cycloalkyl, alkylpyridinyl or alkyl-1H-pyrazolyl;

A compound of formula (I) wherein R⁸ is hydrogen, halogen, alkoxy, haloalkoxy, alkylpyridinyl or alkyl-1H-pyrazolyl;

A compound of formula (I) wherein R⁸ is hydrogen, fluoro, methoxy, trifluoroethoxy, trifluoropropoxy, methylpyridinyl or methyl-1H-pyrazolyl;

A compound of formula (I) wherein R⁹ is hydrogen, alkyl, haloalkyl, cycloalkyl, formyl or alkoxycarbonyl;

A compound of formula (I) wherein R⁹ is hydrogen, alkyl, haloalkyl or alkoxycarbonyl;

A compound of formula (I) wherein R⁹ is hydrogen or alkyl;

A compound of formula (I) wherein R⁹ is hydrogen, methyl, ethyl, tert-butoxycarbonyl or difluoroethyl;

A compound of formula (I) wherein R⁹ is hydrogen, methyl or ethyl;

A compound of formula (I) wherein R⁹ is hydrogen, alkyl, haloalkyl, formyl or alkoxycarbonyl; and A compound of formula (I) wherein R⁹ is hydrogen, methyl, ethyl, difluoroethyl, formyl, methoxycarbonyl or trifluoroethyl.

The invention further relates to a compound of formula (I) selected from:

3-[(2S,4R)-4-(2-Chloro-4-methoxy-benzenesulfonyl)-2-(1-cyano-cyclopropylcarbamoyl)-pyrrolidine-1-carbonyl]-3-(5-chloro-pyridin-2-yl)-azetidine-1-carboxylic acid tert-butyl ester;

(2S,4R)-4-(2-Chloro-4-methoxy-benzenesulfonyl)-1-[3-(5-chloro-pyridin-2-yl)-azetidine-3-carbonyl]-pyrrolidine-2-carboxylic acid (1-cyano-cyclopropyl)-amide;

(2S,4R)-4-(2-Chloro-4-methoxy-benzenesulfonyl)-1-[3-(5-chloro-pyridin-2-yl)-1-methyl-azetidine-3-carbonyl]-pyrrolidine-2-carboxylic acid (1-cyano-cyclopropyl)-amide;

3-(5-Chloro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester;

3-(5-Bromo-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester;

(2S,4R)-1-[3-(5-Chloro-pyridin-2-yl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[3-(5-Bromo-pyridin-2-yl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[3-(5-Chloro-pyridin-2-yl)-1-(2,2-difluoro-ethyl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[3-(5-Bromo-pyridin-2-yl)-1-(2,2-difluoro-ethyl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide;

3-[(2S,4R)-4-(2-Chloro-benzenesulfonyl)-2-(1-cyano-cyclopropylcarbamoyl)-pyrrolidine-1-carbonyl]-3-(5-chloro-3-fluoro-pyridin-2-yl)-azetidine-1-carboxylic acid tert-butyl ester;

tert-Butyl 3-(5-bromo-3-fluoropyridin-2-yl)-3-((2S,4R)-4-(2-chlorophenylsulfonyl)-2-(1-cyanocyclopropylcarbamoyl)pyrrolidine-1-carbonyl)azetidine-1-carboxylate;

(2S,4R)-1-(3-(5-Chloro-3-fluoropyridin-2-yl)azetidine-3-carbonyl)-4-(2-chlorophenylsulfonyl)-N-(1-cyanocyclopropyl)pyrrolidine-2-carboxamide;

(2S,4R)-1-[3-(5-Bromo-3-fluoro-pyridin-2-yl)-azetidine-3-carbonyl]-4-(2-chloro-benzenesulfonyl)-pyrrolidine-2-carboxylic acid (1-cyano-cyclopropyl)-amide;

(2S,4R)-1-[3-(5-Bromo-3-fluoro-pyridin-2-yl)-1-methyl-azetidine-3-carbonyl]-4-(2-chloro-benzenesulfonyl)-pyrrolidine-2-carboxylic acid (1-cyano-cyclopropyl)-amide;

(2S,4R)-1-[3-(5-Bromo-3-fluoro-pyridin-2-yl)-1-ethyl-azetidine-3-carbonyl]-4-(2-chloro-benzenesulfonyl)-pyrrolidine-2-carboxylic acid (1-cyano-cyclopropyl)-amide;

(2S,4R)-4-(2-Chloro-benzenesulfonyl)-1-[3-(5-chloro-3-fluoro-pyridin-2-yl)-1-methyl-azetidine-3-carbonyl]-pyrrolidine-2-carboxylic acid (1-cyano-cyclopropyl)-amide;

3-(5-Chloro-3-fluoro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester;

3-(5-Bromo-3-fluoro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester;

(2S,4R)-1-(3-(5-Bromo-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide;

(2S,4R)-1-(3-(5-Chloro-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide;

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester;

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester;

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester;

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester;

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester;

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester;

tert-Butyl 2-(5-chloro-3-fluoropyridin-2-yl)-2-((2S,4R)-4-(2-chloro-4-((S)-1,1,1-trifluoropropan-2-yloxy)phenylsulfonyl)-2-(1-cyanocyclopropylcarbamoyl)pyrrolidine-1-carbonyl)azetidine-1-carboxylate;

tert-Butyl 2-(5-chloro-3-fluoropyridin-2-yl)-2-((2S,4R)-4-(2-chloro-4-((S)-1,1,1-trifluoropropan-2-yloxy)phenylsulfonyl)-2-(1-cyanocyclopropylcarbamoyl)pyrrolidine-1-carbonyl)azetidine-1-carboxylate;

2-(5-Bromo-3-fluoro-pyridin-2-yl)-2-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester;

2-(5-Bromo-3-fluoro-pyridin-2-yl)-2-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester;

(2S,4R)-4-(2-Chloro-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide;

(2S,4R)-4-(2-Bromo-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide;

3-(5-Bromo-3-fluoro-pyridin-2-yl)-3-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester;

(2S,4R)-1-[3-(5-Bromo-3-fluoro-pyridin-2-yl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-4-(2-Chloro-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-(2-chloro-4-fluoro-benzenesulfonyl)-pyrrolidine-2-carboxylic acid (1-cyano-cyclopropyl)-amide;

(2S,4R)-1-[2-(5-Chloro-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Chloro-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-methyl-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

2-(5-Chloro-3-fluoro-pyridin-2-yl)-2-[(2S,4R)-4-[2-chloro-4-(2-methyl-pyridin-4-yl)-benzenesulfonyl]-2-(1-cyano-cyclopropylcarbamoyl)-pyrrolidine-1-carbonyl]-azetidine-1-carboxylic acid tert-butyl ester;

2-(5-Bromo-3-fluoro-pyridin-2-yl)-2-[(2S,4R)-4-[2-chloro-4-(2-methyl-pyridin-4-yl)-benzenesulfonyl]-2-(1-cyano-cyclopropylcarbamoyl)-pyrrolidine-1-carbonyl]-azetidine-1-carboxylic acid tert-butyl ester;

(2S,4R)-1-[2-(5-Chloro-3-fluoro-pyridin-2-yl)-azetidine-2-carbonyl]-4-[2-chloro-4-(2-methyl-pyridin-4-yl)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-(2-methyl-pyridin-4-yl)-benzenesulfonyl]-pyrrolidine-2-carboxylic acid (1-cyano-cyclopropyl)-amide;

tert-Butyl 2-(5-chloro-3-fluoropyridin-2-yl)-2-((2S,4R)-4-(2-chloro-4-(1-methyl-1H-pyrazol-4-yl)phenylsulfonyl)-2-(1-cyanocyclopropylcarbamoyl)pyrrolidine-1-carbonyl)azetidine-1-carboxylate;

tert-Butyl 2-(5-bromo-3-fluoropyridin-2-yl)-2-((2S,4R)-4-(2-chloro-4-(1-methyl-1H-pyrazol-4-yl)phenylsulfonyl)-2-(1-cyanocyclopropylcarbamoyl)pyrrolidine-1-carbonyl)azetidine-1-carboxylate;

(2S,4R)-1-[2-(5-Chloro-3-fluoro-pyridin-2-yl)-azetidine-2-carbonyl]-4-[2-chloro-4-(1-methyl-1H-pyrazol-4-yl)-benzenesulfonyl]-pyrrolidine-2-carboxylic acid (1-cyano-cyclopropyl)-amide; and (2S,4R)-1-[2-(5-Bromo-3-fluoro-pyridin-2-yl)-azetidine-2-carbonyl]-4-[2-chloro-4-(1-methyl-1H-pyrazol-4-yl)-benzenesulfonyl]-pyrrolidine-2-carboxylic acid (1-cyano-cyclopropyl)-amide.

The invention relates in particular to a compound of formula (I) selected from:

(2S,4R)-4-(2-Chloro-4-methoxy-benzenesulfonyl)-1-[3-(5-chloro-pyridin-2-yl)-azetidine-3-carbonyl]-pyrrolidine-2-carboxylic acid (1-cyano-cyclopropyl)-amide;

(2S,4R)-1-(3-(5-chloro-3-fluoropyridin-2-yl)azetidine-3-carbonyl)-4-(2-chlorophenylsulfonyl)-N-(1-cyanocyclopropyl)pyrrolidine-2-carboxamide;

(2S,4R)-1-[3-(5-Bromo-3-fluoro-pyridin-2-yl)-azetidine-3-carbonyl]-4-(2-chloro-benzenesulfonyl)-pyrrolidine-2-carboxylic acid (1-cyano-cyclopropyl)-amide;

(2S,4R)-1-[3-(5-Bromo-3-fluoro-pyridin-2-yl)-1-methyl-azetidine-3-carbonyl]-4-(2-chloro-benzenesulfonyl)-pyrrolidine-2-carboxylic acid (1-cyano-cyclopropyl)-amide;

(2S,4R)-1-[3-(5-Bromo-3-fluoro-pyridin-2-yl)-1-ethyl-azetidine-3-carbonyl]-4-(2-chloro-benzenesulfonyl)-pyrrolidine-2-carboxylic acid (1-cyano-cyclopropyl)-amide;

(2S,4R)-4-(2-Chloro-benzenesulfonyl)-1-[3-(5-chloro-3-fluoro-pyridin-2-yl)-1-methyl-azetidine-3-carbonyl]-pyrrolidine-2-carboxylic acid (1-cyano-cyclopropyl)-amide;

(2S,4R)-1-(3-(5-Bromo-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide;

(2S,4R)-1-(3-(5-Chloro-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide;

(2S,4R)-4-(2-Bromo-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide;

(2S,4R)-1-[3-(5-Bromo-3-fluoro-pyridin-2-yl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Chloro-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-methyl-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-(2-methyl-pyridin-4-yl)-benzenesulfonyl]-pyrrolidine-2-carboxylic acid (1-cyano-cyclopropyl)-amide; and (2S,4R)-1-[2-(5-Chloro-3-fluoro-pyridin-2-yl)-azetidine-2-carbonyl]-4-[2-chloro-4-(1-methyl-1H-pyrazol-4-yl)-benzenesulfonyl]-pyrrolidine-2-carboxylic acid (1-cyano-cyclopropyl)-amide.

The invention further relates in particular to a compound of formula (I) selected from:

(2S,4R)-1-[3-(5-Bromo-3-fluoro-pyridin-2-yl)-1-(2,2-difluoro-ethyl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-formyl-azetidine-3-carbonyl]-4-[2-chloro-4-((S)-2,2,2-trifluoro- 1-methyl-ethoxy)-benzenesulfonyl]-pyrrolidine-2-carboxylic acid (1-cyano-cyclopropyl)-amide;

3-(5-Bromo-3-fluoro-pyridin-2-yl)-3-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid methyl ester; and (2S,4R)-1-[3-(5-Bromo-3-fluoro-pyridin-2-yl)-1-(2,2,2-trifluoro-ethyl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide.

The compound of formula (I) can be prepared using procedures known in the art. The compound of formula (I) can also be prepared using the following procedures.

The following abbreviations are used in the present specification.

AcOEt: Ethyl acetate;
ACN: Acetonitrile;
BOP: Benzotriazolyl-N-oxy-tris(dimethylamino)-phosphonium hexafluorophosphate;
BOP-Cl: Bis-(2-oxo-3-oxazolidinyl)-phosphinic acid chloride;
CDI: 1,1'-Carbonyldiimidazole;
DCM: Dichloromethane
DIEA: Diisopropyl ethyl amine;
DMF: N,N-Dimethylformamide;
EDCI: N-(3-Dimethylaminopropyl)-N'-ethyl-carbodiimide hydrochloride;
h: hour
HATU: O-(7-azabenzotriazol-1-yl)-1,1,3,3-tetramethyluronium hexafluorophosphate;
HOBT: 1-Hydroxybenzotriazole;
Hunig's Base: Ethyl-diisopropyl-amine;
KHMDS: Potassium bis(trimethylsilyl)amide
LDA: Lithiumdiisopropylamide
LHMDS: Lithium bis(trimethylsilyl)amide
MeOH: Methanol
Mes-Cl: Mesyl chloride;
min: minute
Na$_2$SO$_4$: Sodium sulfate
Nos-Cl: 3-Nitrobenzenesulfonyl chloride;
Pd$_2$(dba)$_3$: Tris(dibenzylideneacetone)dipalladium
PyBOP: Benzotriazol-1-yl-oxytripyrrolidinephosphonium hexafluorophosphate;
TBTU: O-(Benzotriazol-1-yl)-N,N,N',N'-tetramethyluronium terafluoroborate;
THF: Tetrahydrofurane;
TFA: Trifluoroacetic acid; and
Tos-Cl: Toluene-4-sulfonyl chloride.

Scheme 1

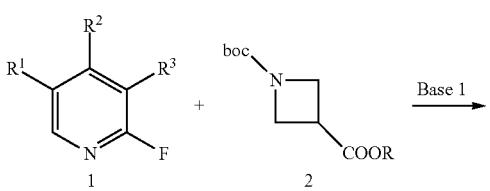

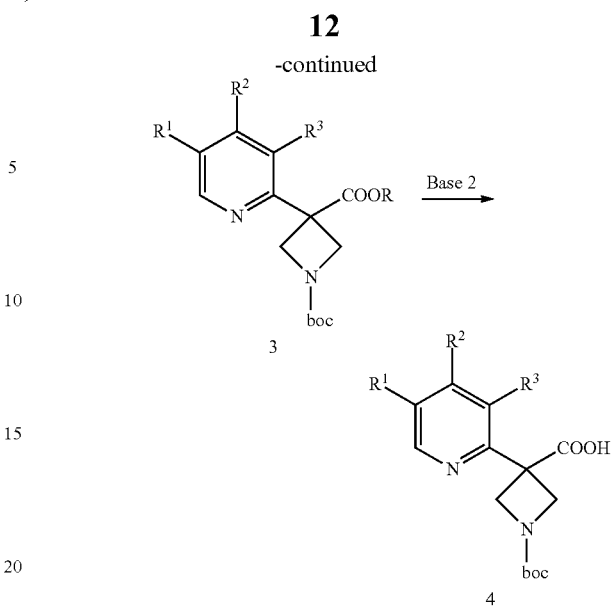

R$^1$-R$^3$ are as defined above; R is e.g. Methyl, Ethyl, iPropyl or Benzyl; Base 1 is e.g. NaOtBu, KOtBu, NaH, LiHMDS, KHMDS or LDA; Base 2 is e.g. LiOH, NaOH or KOH.

A 2-fluoro pyridine derivative such as 1 is treated with a Boc-protected azetidine derivative 2 in the presence of a base (Base 1 as defined above) to yield the azetidine derivative 3. Compound 3 is treated with a base (Base 2 as defined above) to yield the final carboxylic acid derivative 4 as free acid or as a salt thereof.

Scheme 2

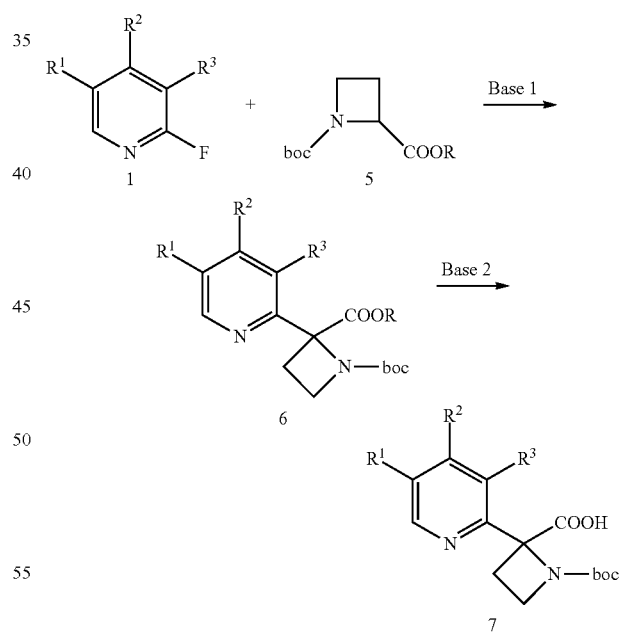

R$^1$-R$^3$ are as defined above; R is e.g. Methyl, Ethyl, iPropyl or Benzyl; Base 1 is e.g. NaOtBu, KOtBu, NaH, LiHMDS, KHMDS or LDA; Base 2 is e.g. LiOH, NaOH or KOH.

A 2-fluoro pyridine derivative such as 1 is treated with a Boc-protected azetidine derivative 5 in the presence of a base (Base 1 as defined above) to yield the azetidine derivative 6. Compound 6 is treated with a base (Base 2 as defined above) to yield the final carboxylic acid derivative 4 as free acid or as a salt thereof.

Scheme 3

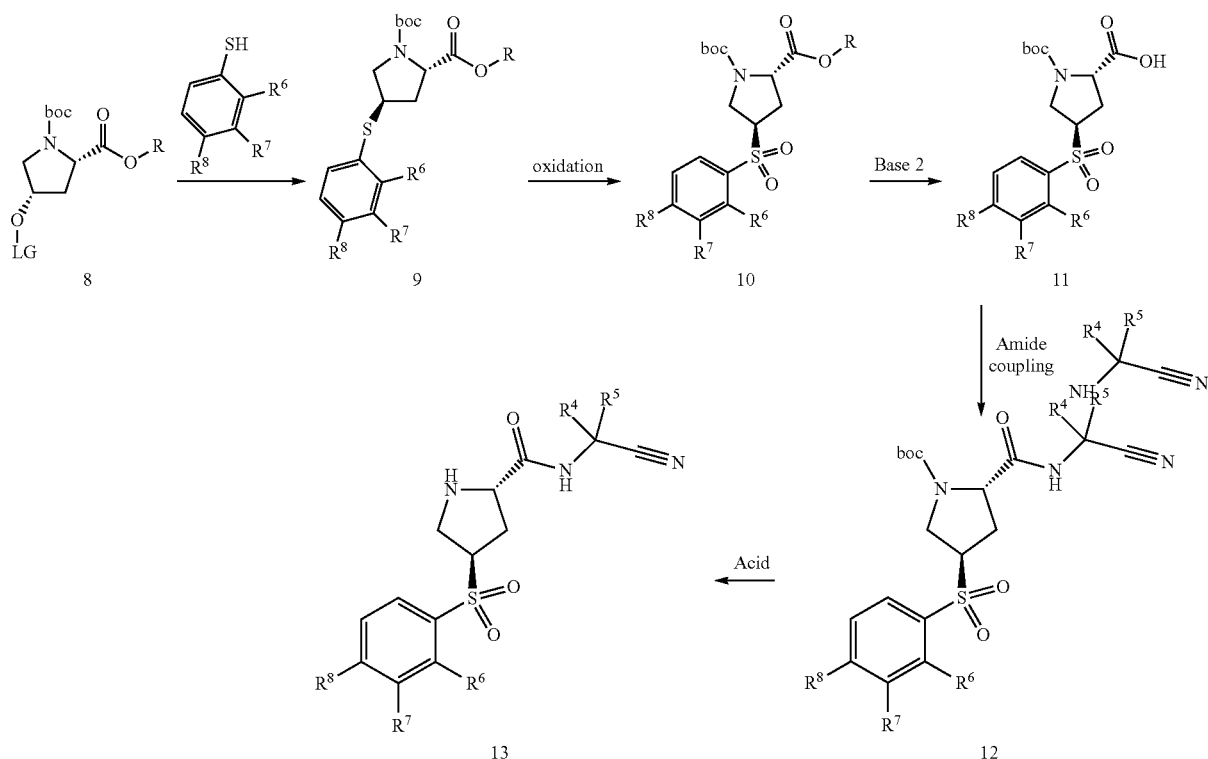

LG is a leaving group such as triflate, mesylate, tosylate, brosylate or nosylate; $R^4$-$R^8$ are as defined above; R is e.g. Methyl, Ethyl, iPropyl or Benzyl.

A Boc-protected proline derivative 8 is reacted with a 2-chlorophenylthiol derivative in the presence of a base such as triethyl amine, DIEA, 2,6-lutidine, etc. To yield the thio-ether derivative 9. Oxidation of 9 with a peroxide reagent such as $H_2O_2$, oxone, MCPBA yields the sulfone derivative 10. Saponification of the ester to the acid with a base such as LiOH, NaOH, KOH, etc. yields the corresponding carboxylic acid 11 or salts thereof. Amide coupling is accomplished by reaction of 11 with 1-amino-cyclopropane-carbonitrile and a coupling reagent such as EDCI, CDI, BOP-Cl, TBTU, HATU, PyBOP, BOP etc. in the presence of a base such as DIEA, triethyl amine, lutidine, etc. to yield amide 12. Finally, the Boc-protecting group is removed by treating compound 12 with an acid such as TFA, HCl in an organic solvent (e.g. AcOEt, dioxane) or formic acid to yield amine 13.

Scheme 4

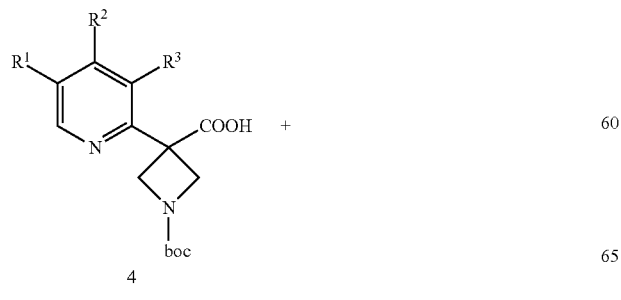

-continued

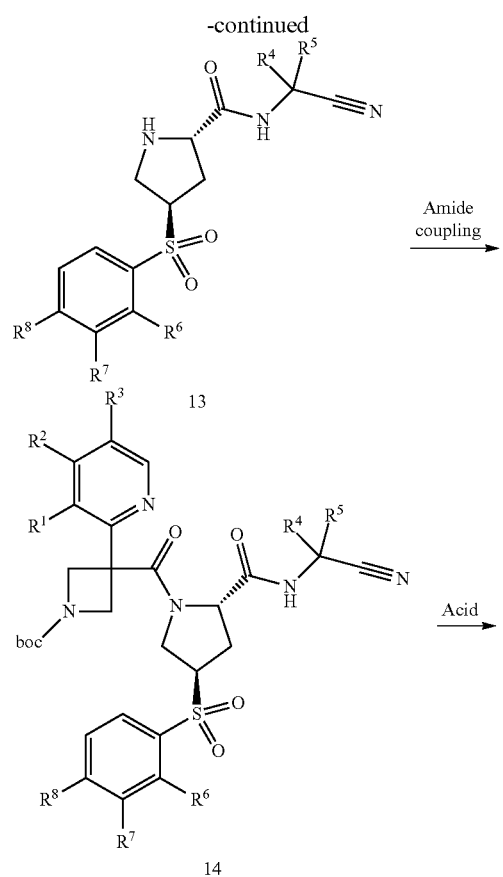

15

-continued

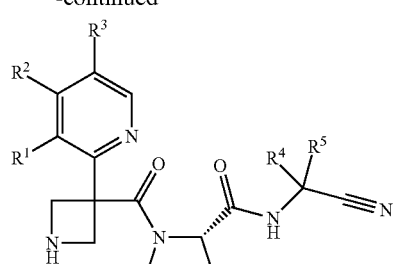

15

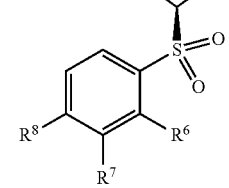

16

Alkylation: R⁹—X
or Reductive amination: R¹⁰—C(O)—Y

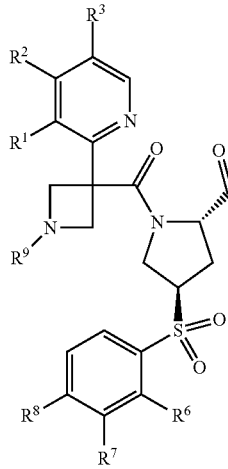

16

R¹-R⁹ are as defined above; Acid is e.g. TFA, HCl or formic acid; X is a leaving group such as Cl, Br, I, triflate, mesylate, tosylate, phenylsulfonate, brosylate or nosylate; R¹⁰ is e.g. alkyl, haloalkyl or cycloalkyl; Y is e.g. H, alkyl or haloalkyl.

Carboxylic acid 4 is reacted with amine 13 in the presence of one of the amide coupling reagents such as EDCI, CDI, BOP-Cl, TBTU, HATU, PyBOP, BOP etc. in the presence of a base such as DIEA, triethyl amine, 2,6-lutidine, etc. to yield amide 14. Compound 14 is deprotected with an acid such as TFA, formic acid, HCl in an organic solvent (e.g. dioxane, AcOEt) to yield amine 15. The amine 15 can be alkylated with an alkylating agent R⁹—X such as alkyl halides, sulfonates, etc. or alternatively by reductive amination to yield amine 16. In the latter case R¹⁰—C(O)—Y is an adehyde or ketone; R¹⁰ is e.g. alkyl, haloalkyl or cycloalkyl; Y is e.g. hydrogen, alkyl or haloalkyl; reducing agents are e.g. NaBH₄, NaCNBH₃ or sodium triacetoxyborohydride.

16

Scheme 5

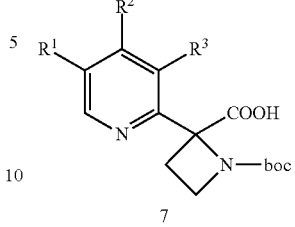

7

+

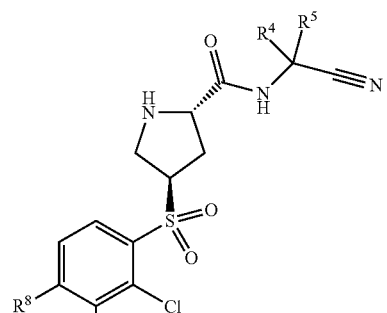

13

Amide coupling

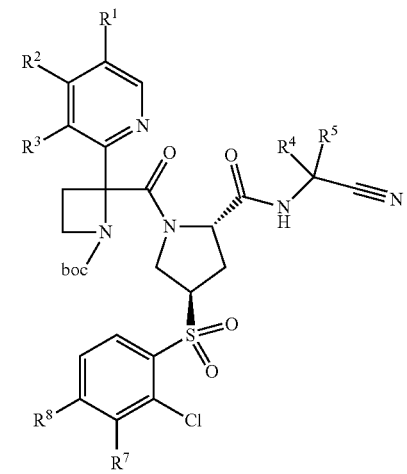

14

Acid

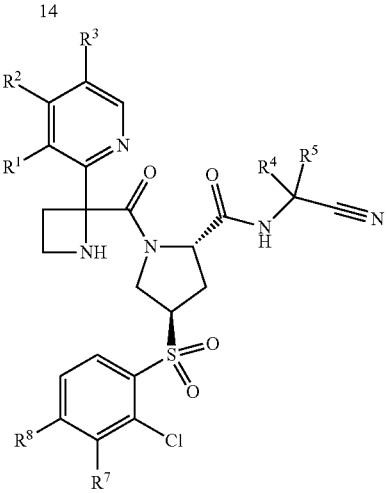

18

R¹-R⁸ are as defined above; Acid is e.g. TFA, HCl or formic acid.

Carboxylic acid 7 is reacted with amine 13 in the presence of one of the amide coupling reagents such as EDCI, CDI, BOP-Cl, TBTU, HATU, PyBOP, BOP etc. in the presence of a base such as DIEA, triethyl amine, lutidine, etc. to yield amide 17. Compound 18 is deprotected with an acid such as TFA, formic acid, HCl in an organic solvent (e.g. dioxane, AcOEt) to yield amine 18.

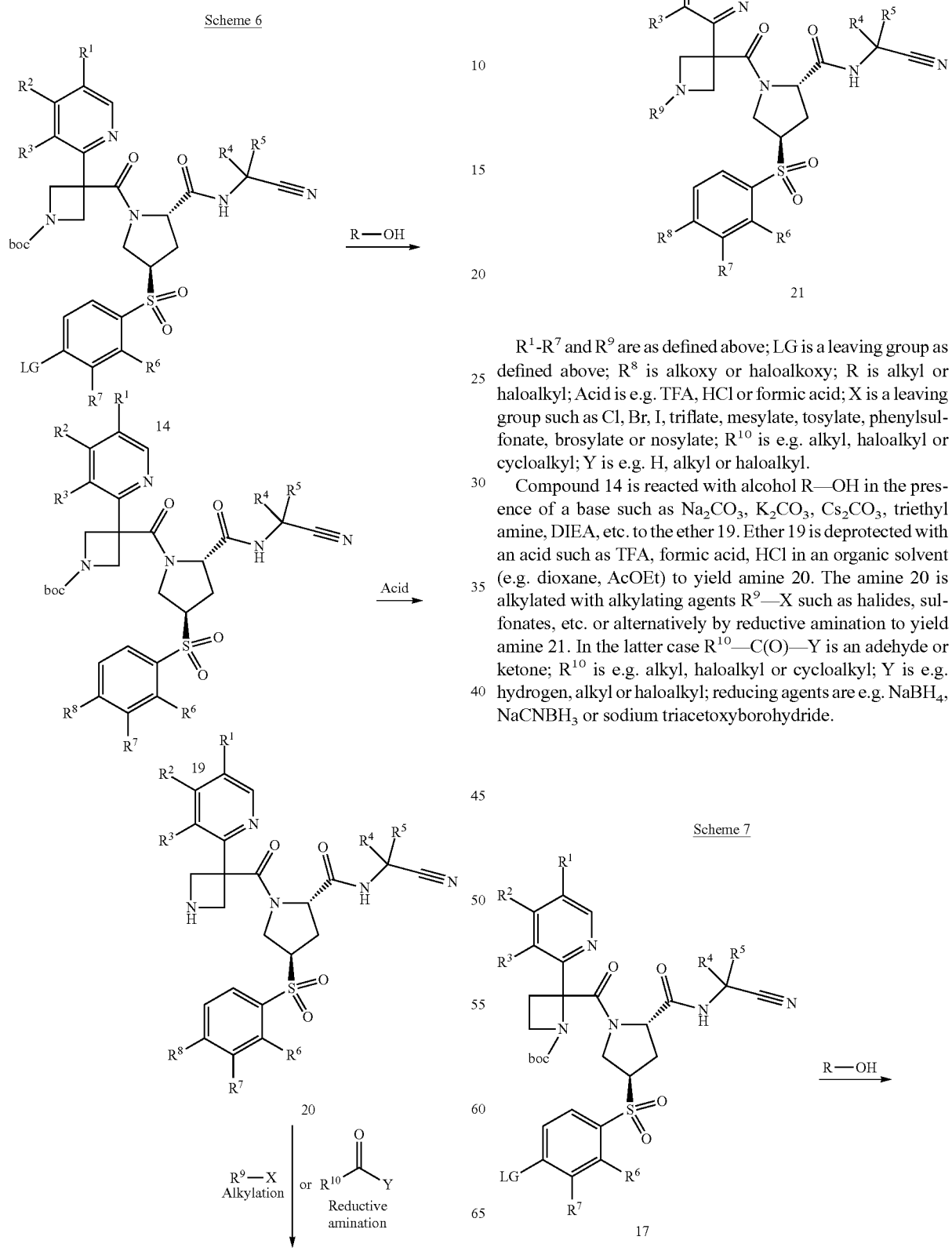

$R^1$-$R^7$ and $R^9$ are as defined above; LG is a leaving group as defined above; $R^8$ is alkoxy or haloalkoxy; R is alkyl or haloalkyl; Acid is e.g. TFA, HCl or formic acid; X is a leaving group such as Cl, Br, I, triflate, mesylate, tosylate, phenylsulfonate, brosylate or nosylate; $R^{10}$ is e.g. alkyl, haloalkyl or cycloalkyl; Y is e.g. H, alkyl or haloalkyl.

Compound 14 is reacted with alcohol R—OH in the presence of a base such as $Na_2CO_3$, $K_2CO_3$, $Cs_2CO_3$, triethyl amine, DIEA, etc. to the ether 19. Ether 19 is deprotected with an acid such as TFA, formic acid, HCl in an organic solvent (e.g. dioxane, AcOEt) to yield amine 20. The amine 20 is alkylated with alkylating agents $R^9$—X such as halides, sulfonates, etc. or alternatively by reductive amination to yield amine 21. In the latter case $R^{10}$—C(O)—Y is an adehyde or ketone; $R^{10}$ is e.g. alkyl, haloalkyl or cycloalkyl; Y is e.g. hydrogen, alkyl or haloalkyl; reducing agents are e.g. $NaBH_4$, $NaCNBH_3$ or sodium triacetoxyborohydride.

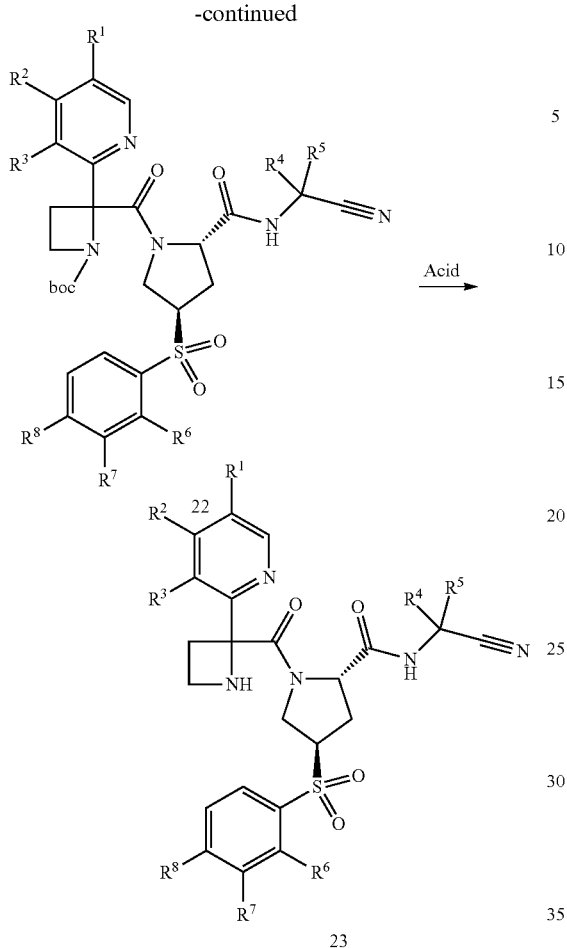

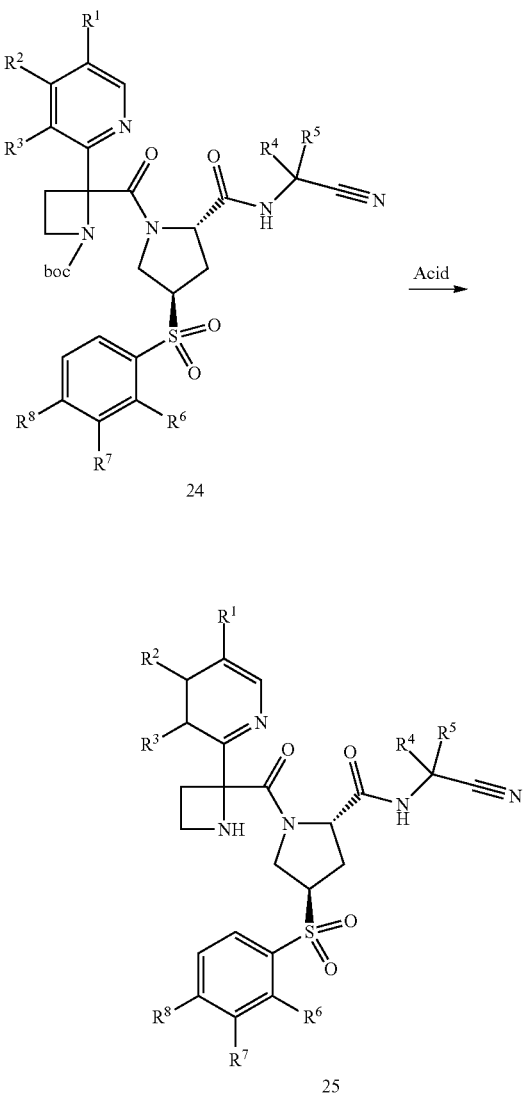

R¹-R⁷ are as defined above; LG is a leaving group as defined above; R⁸ is alkoxy or haloalkoxy; R is alkyl or haloalkyl; Acid is e.g. TFA, HCl or formic acid.

Compound 17 is reacted with alcohol R—OH in the presence of a base such as Na$_2$CO$_3$, K$_2$CO$_3$, Cs$_2$CO$_3$, triethyl amine, DIEA, etc. to the ether 22. Ether 22 is deprotected with an acid such as TFA, formic acid, HCl in an organic solvent (e.g. dioxane, AcOEt) to yield amine 23.

Scheme 8

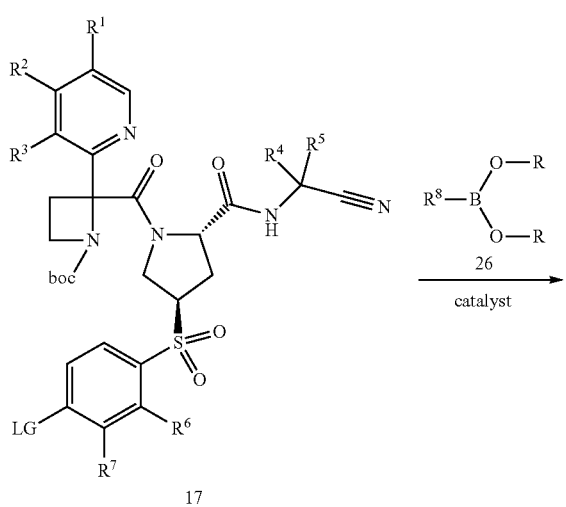

R¹-R⁷ are as defined above; LG is a leaving group such as Cl, Br, I; R⁸ is phenyl, substituted phenyl, heterocyclyl or substituted heterocyclyl as defined above; R is H or Methyl, or both R together with the boron atom to which they are attached form a ring such as 2,4,4,5,5-pentamethyl-[1,3,2] dioxaborolane; Acid is e.g. TFA, HCl or formic acid.

Compound 17 is reacted with a boronic acid or ester derivative 26 in the presence of a base such as Na$_2$CO$_3$, K$_2$CO$_3$, Cs$_2$CO$_3$, KOtBu, K$_3$PO$_4$, etc. and a catalyst known in the art for performing Suzuki reactions such as e.g. Pd(PPh$_3$)$_4$, Pd$_2$(dba)$_3$ with a phosphine ligand, etc. to yield the biaryl derivative 24. Compound 24 is deprotected with an acid such as TFA, formic acid, HCl in an organic solvent (e.g. dioxane, AcOEt) to yield amine 25.

The invention also relates to a process for the preparation of a compound of formula (I) as defined above, comprising one of the following steps:

(a) The reaction of a compound of formula (II)

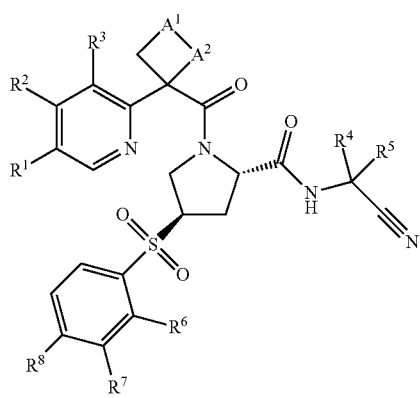

in the presence of acid, wherein $R^1$ to $R^8$ are as defined above, one of $A^1$ and $A^2$ is —$CH_2$— and the other one is —$NR^{10}$— wherein $R^{10}$ is an amine protecting group;

(b) The reaction of a compound of formula (III)

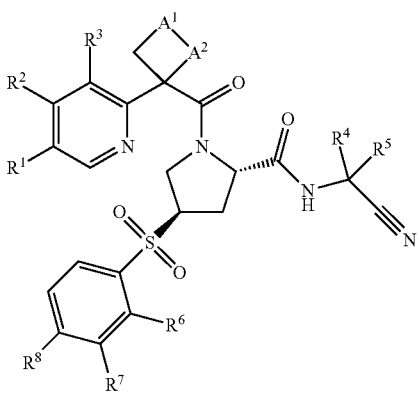

in the presence of $R^9$—X, wherein $A^1$, $A^2$ and $R^1$ to $R^9$ are as defined above; or (c) The reaction of a compound of formula (III) as defined above in the presence of $R^{10}$—C(O)—Y and a reducing agent, wherein $A^1$, $A^2$ and $R^1$ to $R^9$ are as defined above, $R^{10}$ is alkyl, haloalkyl or cycloalkyl and Y is hydrogen, alkyl or haloalkyl.

In step (a), the acid is for example TFA, HCl or formic acid.

In step (b), the amine protecting group is for example Boc, Fmoc, Cbz, Teoc, benzyl, or Moz.

In step (c), the reducing agent is for example $NaBH_4$, $NaCNBH_3$ or sodium triacetoxyborohydride.

A compound of formula (I), when manufactured according to the above process is also an object of the invention.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The invention thus also relates in particular to the following:

A compound of formula (I) for use as therapeutically active substance;

A pharmaceutical composition comprising a compound of formula (I) and a therapeutically inert carrier;

The use of a compound of formula (I) for the preparation of a medicament for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration;

A compound of formula (I) for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration; and A method for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration, which method comprises administering an effective amount of a compound of formula (I).

The invention will be illustrated by the following examples which have no limiting character.

EXAMPLES

Example 1

3-[(2S,4R)-4-(2-Chloro-4-methoxy-benzenesulfonyl)-2-(1-cyano-cyclopropylcarbamoyl)-pyrrolidine-1-carbonyl]-3-(5-chloro-pyridin-2-yl)-azetidine-1-carboxylic acid tert-butyl ester

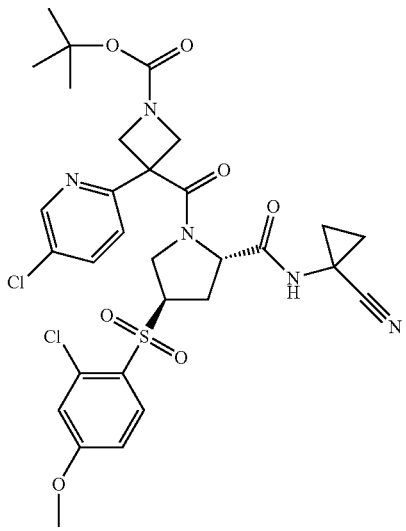 [SMILES: COc1ccc(S(=O)(=O)[C@@H]2C[C@@H](C(=O)NC3(C#N)CC3)N(C(=O)C3(c4ccc(Cl)cn4)CN(C(=O)OC(C)(C)C)C3)C2)c(Cl)c1]

A) 3-(5-Chloro-pyridin-2-yl)-azetidine-1,3-dicarboxylic acid 1-tert-butyl ester 3-methyl ester

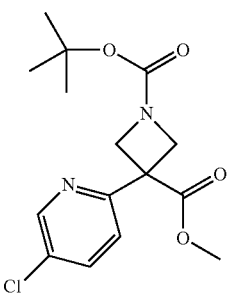 [SMILES: COC(=O)C1(c2ccc(Cl)cn2)CN(C(=O)OC(C)(C)C)C1]

To a solution of 5-chloro-2-fluoropyridine (0.5 g, 3.8 mmol, Eq: 1.00) and 1-tert-butyl 3-methyl azetidine-1,3-dicarboxylate (818 mg, 3.8 mmol, Eq: 1.00) in toluene (5 ml) was added dropwise at 0° C. for 15 min a 0.5 M solution of KHMDS (7.6 ml, 3.8 mmol, Eq: 1.00) in toluene. The colorless solution turned into yellow-orange. After stirring at 0° C. for 45 min, the reaction mixture was allowed to warm to 20° C. and stirred for 2.5 h. A saturated aqueous NH$_4$Cl solution (50 ml) was added and the aqueous phase was extracted with AcOEt (2×75 ml). The combined organic layers were washed with brine, dried over Na$_2$SO$_4$, filtered and concentrated under reduced pressure. The crude material was purified by flash chromatography (silica gel, 12 g, 10% to 60% AcOEt in heptane) to yield a colorless gum (0.234 g; 19%). m/z=327.2 [M+H]$^+$.

B) Lithium 1-tert-butoxycarbonyl-3-(5-chloro-pyridin-2-yl)-azetidine-3-carboxylate

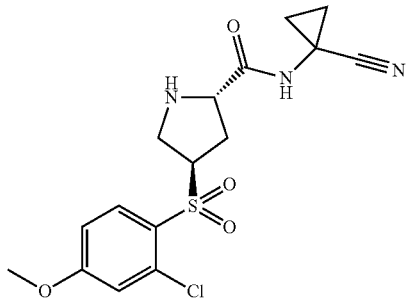 [SMILES: COc1ccc(S(=O)(=O)[C@H]2CN[C@H](C(=O)NC3(C#N)CC3)C2)c(Cl)c1]

In a 10 ml round-bottomed flask, example 1A) (0.21 g, 643 µmol, Eq: 1.00) and lithium hydroxide (24.6 mg, 1.03 mmol, Eq: 1.6) were combined with tetrahydrofurane (1.8 ml) and water (1.2 ml) to give a light yellow suspension. The reaction mixture was stirred at 22° C. for 2 h. The crude reaction mixture was concentrated in vacuo to yield an off-white solid (0.241 g; 100%). m/z=311.3 [M−H]$^−$.

C) (2S,4R)-4-(2-Chloro-4-methoxy-benzenesulfonyl)-pyrrolidine-2-carboxylic acid (1-cyano-cyclopropyl)-amide In a 10 ml round-bottomed flask, CAS #1252640-17-7 (0.25 g, 517 µmol, Eq: 1.00) and 4 M hydrogen chloride solution in dioxane (517 µl, 2.07 mmol, Eq: 4) were combined to give a colorless solution. The reaction mixture was stirred at 22° C. for 1.5 h. After stirring for 20 min, a slurry was formed. The crude reaction mixture was diluted in AcOEt (30 ml) and extracted with aqueous 10% Na$_2$CO$_3$-solution (20 ml). The aqueous layer was back-extracted with AcOEt (2×20 ml). The organic layers were combined, washed with brine (1×15 ml), dried over Na$_2$SO$_4$ and concentrated in vacuo to yield a colorless foam (202 mg; 100%). m/z=384.3 [M+H]$^+$.

D) 3-[(2S,4R)-4-(2-Chloro-4-methoxy-benzenesulfonyl)-2-(1-cyano-cyclopropylcarbamoyl)-pyrrolidine-1-carbonyl]-3-(5-chloro-pyridin-2-yl)-azetidine-1-carboxylic acid tert-butyl ester

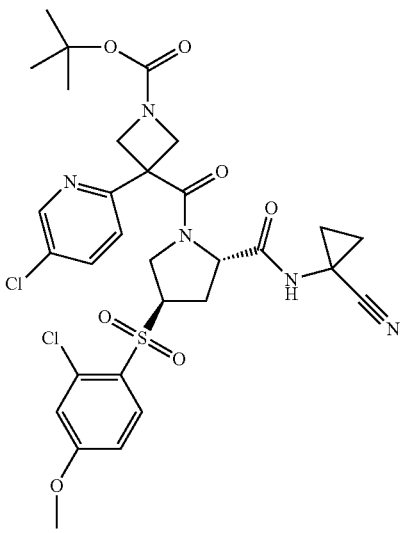 [SMILES: COc1ccc(S(=O)(=O)[C@@H]2C[C@@H](C(=O)NC3(C#N)CC3)N(C(=O)C3(c4ccc(Cl)cn4)CN(C(=O)OC(C)(C)C)C3)C2)c(Cl)c1]

In a 10 ml round-bottomed flask, example 1B) (0.165 g, 518 µmol, Eq: 1.00), HATU (394 mg, 1.04 mmol, Eq: 2) and DIPEA (134 mg, 181 µl, 1.04 mmol, Eq: 2) were combined with acetonitrile (3 ml) to give a light brown solution. Example 1C) (199 mg, 518 µmol, Eq: 1.00) was added to the above solution and stirred at 20° C. for 18 h. The crude reaction mixture was concentrated in vacuo, the residue was diluted with AcOEt (30 ml) and extracted with aqueous 10% $Na_2CO_3$-solution (25 ml), The aqueous layer was back-extracted with AcOEt (2×20 ml), washed with brine, dried over $Na_2SO_4$ and evaporated to dryness. The crude product was subsequently purified by flash chromatography (silica gel, 12 g, 30% to 90% AcOEt in heptane) to yield an off-white foam (0.166 g; 48%). m/z=678.3 [M+H]$^+$.

Example 2

(2S,4R)-4-(2-Chloro-4-methoxy-benzenesulfonyl)-1-[3-(5-chloro-pyridin-2-yl)-azetidine-3-carbonyl]-pyrrolidine-2-carboxylic acid (1-cyano-cyclopropyl)-amide

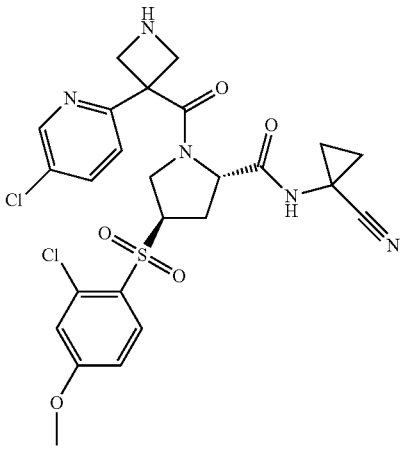 [SMILES: COc1ccc(S(=O)(=O)[C@@H]2C[C@@H](C(=O)NC3(C#N)CC3)N(C(=O)C3(c4ccc(Cl)cn4)CNC3)C2)c(Cl)c1]

In a 10 ml round-bottomed flask, example 1D) (0.15 g, 221 µmol, Eq: 1.00) and formic acid (305 mg, 254 µl, 6.63 mmol, Eq: 30) were combined to give a yellow solution. The mixture was stirred at 20° C. for 20 h. The reaction mixture was diluted with water (2 ml), adjusted to pH=8 with icecold aqueous 10% $Na_2CO_3$-solution, extracted with $CH_2Cl_2$ twice, the combined organic layers were washed with brine, dried over $Na_2SO_4$, filtered and evaporated to yield a light yellow solid (0.131 g; 100%). m/z=580.3 [M+H]$^+$.

Example 3

(2S,4R)-4-(2-Chloro-4-methoxy-benzenesulfonyl)-1-[3-(5-chloro-pyridin-2-yl)-1-methyl-azetidine-3-carbonyl]-pyrrolidine-2-carboxylic acid (1-cyano-cyclopropyl)-amide

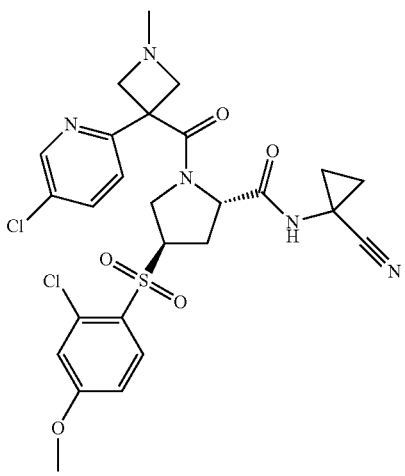 [SMILES: COc1ccc(S(=O)(=O)[C@@H]2C[C@@H](C(=O)NC3(C#N)CC3)N(C(=O)C3(c4ccc(Cl)cn4)CN(C)C3)C2)c(Cl)c1]

To a solution of example 2 (0.05 g, 86.4 µmol, Eq: 1.00) in refluxing methanol (1 ml) was added methyl iodide (9.2 mg, 4.05 µl, 64.8 µmol, Eq: 0.75). After complete addition the mixture was stirred at 80° C. for 2 h. Additional methyl iodide (9.2 mg, 4.05 µl, 64.8 µmol, Eq: 0.75) was added and the mixture was stirred at 80° C. for 2 h, then at 20° C. over night. The mixture was purified by preparative HPLC to yield a colorless solid (3 mg; 6%). m/z=592.2 [M+H]$^+$.

Example 4

3-(5-Chloro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester

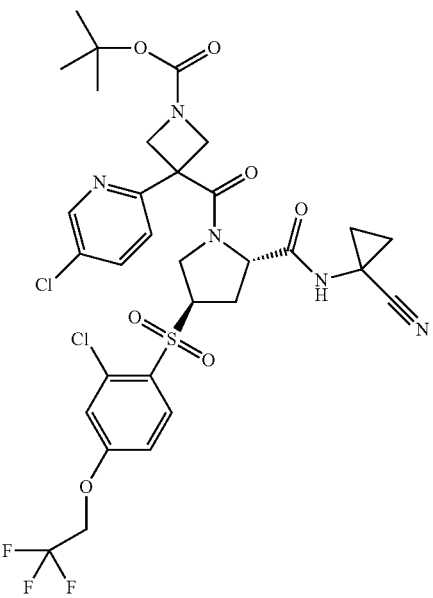 [SMILES: CC(C)(C)OC(=O)N1CC(C(=O)N2C[C@H](S(=O)(=O)c3ccc(OCC(F)(F)F)cc3Cl)C[C@H]2C(=O)NC2(C#N)CC2)(c2ccc(Cl)cn2)C1]

The title compound was prepared in analogy to example 1 starting from CAS #1252634-04-0 to yield a colorless amorphous solid. m/z=746.1 [M+H]$^+$.

Example 5

3-(5-Bromo-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester

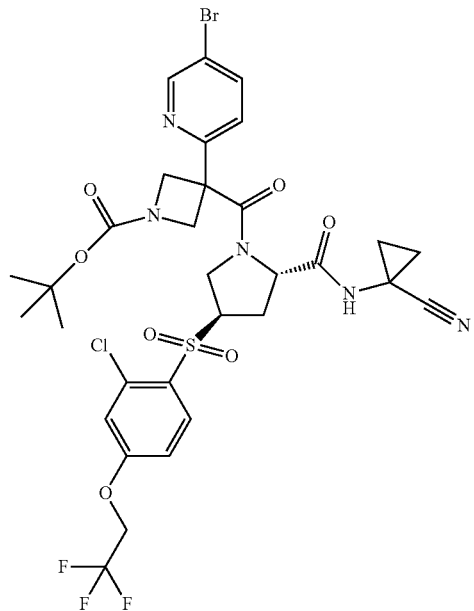 [SMILES: CC(C)(C)OC(=O)N1CC(C(=O)N2C[C@H](S(=O)(=O)c3ccc(OCC(F)(F)F)cc3Cl)C[C@H]2C(=O)NC2(C#N)CC2)(c2ccc(Br)cn2)C1]

The title compound was prepared in analogy to the methods described in example 1 starting from 5-bromo-2-fluoro-pyridine and CAS#1252634-04-0 to yield a yellow foam. m/z=792.1 [M+H]$^+$.

Example 6

(2S,4R)-1-[3-(5-Chloro-pyridin-2-yl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide

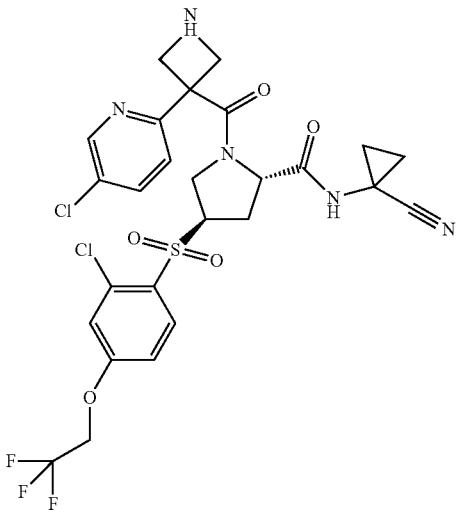 [SMILES: N#CC1(NC(=O)[C@@H]2C[C@@H](S(=O)(=O)c3ccc(OCC(F)(F)F)cc3Cl)CN2C(=O)C2(c3ccc(Cl)cn3)CNC2)CC1]

The title compound was prepared in analogy to example 2 starting from example 4 to yield a colorless waxy solid. m/z=646.1 [M+H]$^+$.

Example 7

(2S,4R)-1-[3-(5-Bromo-pyridin-2-yl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide

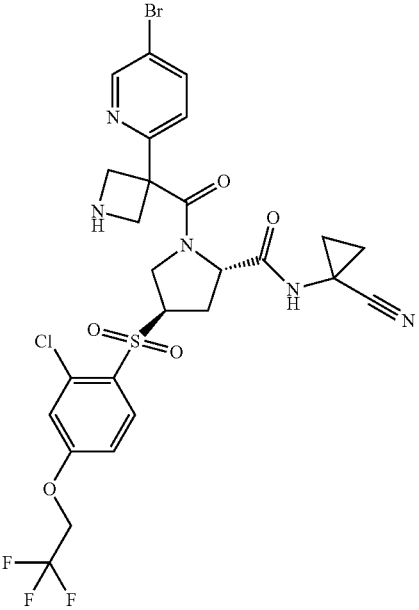 [SMILES: N#CC1(NC(=O)[C@@H]2C[C@@H](S(=O)(=O)c3ccc(OCC(F)(F)F)cc3Cl)CN2C(=O)C2(c3ccc(Br)cn3)CNC2)CC1]

The title compound was prepared in analogy to example 2 starting from example 5 to yield a yellow foam. m/z=692.0 [M+H]$^+$.

Example 8

(2S,4R)-1-[3-(5-Chloro-pyridin-2-yl)-1-(2,2-difluoro-ethyl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide

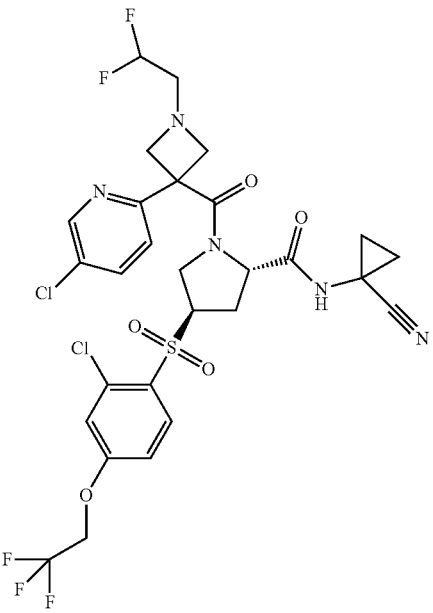 [SMILES: N#CC1(NC(=O)[C@@H]2C[C@@H](S(=O)(=O)c3ccc(OCC(F)(F)F)cc3Cl)CN2C(=O)C2(c3ccc(Cl)cn3)CN(CC(F)F)C2)CC1]

In a 10 ml round-bottomed flask, example 6 (0.082 g, 127 μmol, Eq: 1.00), 2,2-difluoroethyl trifluoromethanesulfonate (40.7 mg, 27.0 μl, 190 μmol, Eq: 1.5) and DIEA (24.6 mg, 33.2 μl, 190 μmol, Eq: 1.5) were combined with acetonitrile (1.5 ml) to give a light yellow solution. The reaction mixture was stirred at 22° C. for 72 h. The crude reaction mixture was concentrated in vacuo and purified by flash chromatography (silica gel, 12 g, 25% to 80% AcOEt in heptane) to yield the title compound as a colorless amorphous solid (0.014 g; 16%). m/z=710.2 [M+H]$^+$.

Example 9

(2S,4R)-1-[3-(5-Bromo-pyridin-2-yl)-1-(2,2-difluoro-ethyl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide

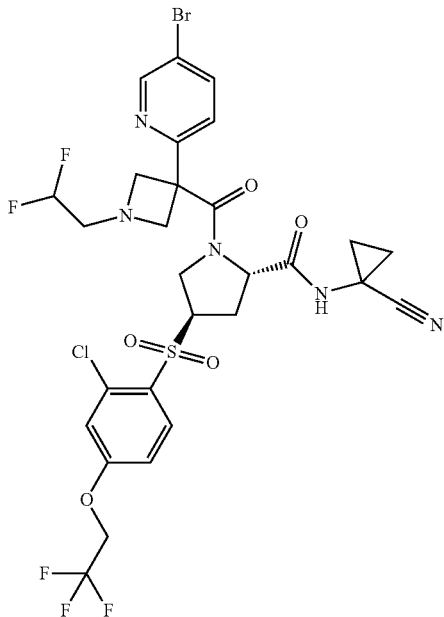 [SMILES: N#CC1(NC(=O)[C@@H]2C[C@@H](S(=O)(=O)c3ccc(OCC(F)(F)F)cc3Cl)CN2C(=O)C2(c3ccc(Br)cn3)CN(CC(F)F)C2)CC1]

The title compound was prepared in analogy to example 8 starting from example 7 to yield a colorless amorphous solid. m/z=756.1 [M+H]$^+$.

Example 10

3-[(2S,4R)-4-(2-Chloro-benzenesulfonyl)-2-(1-cyano-cyclopropylcarbamoyl)-pyrrolidine-1-carbonyl]-3-(5-chloro-3-fluoro-pyridin-2-yl)-azetidine-1-carboxylic acid tert-butyl ester

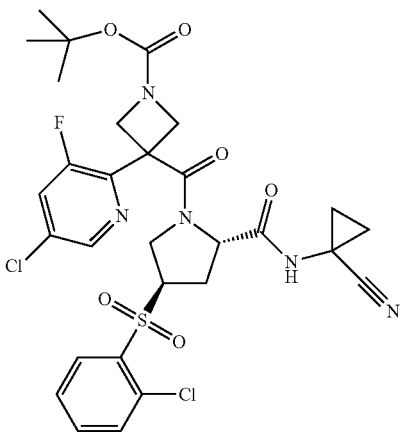 [SMILES: CC(C)(C)OC(=O)N1CC(C(=O)N2C[C@H](S(=O)(=O)c3ccccc3Cl)C[C@H]2C(=O)NC2(C#N)CC2)(c2ncc(Cl)cc2F)C1]

The title compound was prepared in analogy to the methods described for example 1 starting from 5-chloro-2,3-difluoro-pyridine and CAS#1252638-10-0 to yield a colorless foam. m/z=666.2 [M+H]$^+$.

Example 11 tert-Butyl 3-(5-bromo-3-fluoropyridin-2-yl)-3-((2S,4R)-4-(2-chlorophenylsulfonyl)-2-(1-cyanocyclopropylcarbamoyl)pyrrolidine-1-carbonyl)azetidine-1-carboxylate

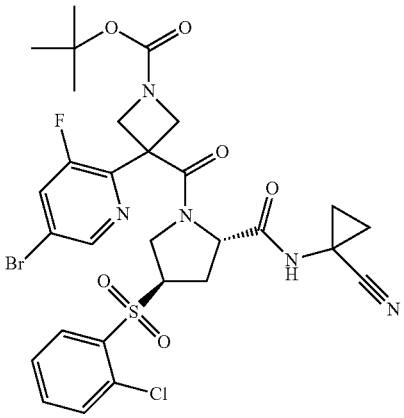 [SMILES: CC(C)(C)OC(=O)N1CC(C(=O)N2C[C@H](S(=O)(=O)c3ccccc3Cl)C[C@H]2C(=O)NC2(C#N)CC2)(c2ncc(Br)cc2F)C1]

The title compound was prepared in analogy to the methods described for example 1 starting from 5-bromo-2,3-difluoro-pyridine and CAS#1252638-10-0 to yield a colorless foam. m/z=712.0 [M+H]$^+$.

Example 12

(2S,4R)-1-(3-(5-Chloro-3-fluoropyridin-2-yl)azetidine-3-carbonyl)-4-(2-chlorophenylsulfonyl)-N-(1-cyanocyclopropyl)pyrrolidine-2-carboxamide

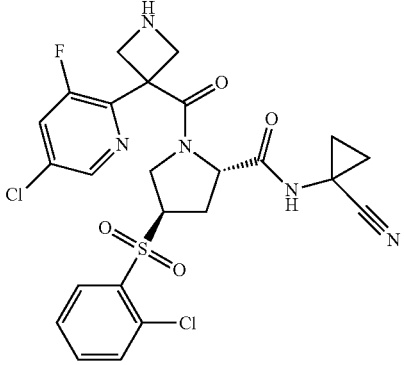 [SMILES: N#CC1(NC(=O)[C@@H]2C[C@@H](S(=O)(=O)c3ccccc3Cl)CN2C(=O)C2(c3ncc(Cl)cc3F)CNC2)CC1]

The title compound was prepared in analogy to the methods described for example 2 starting from example 10 to yield a colorless foam. m/z=566.1 [M+H]+.

Example 13

(2S,4R)-1-[3-(5-Bromo-3-fluoro-pyridin-2-yl)-azetidine-3-carbonyl]-4-(2-chloro-benzenesulfonyl)-pyrrolidine-2-carboxylic acid (1-cyano-cyclopropyl)-amide

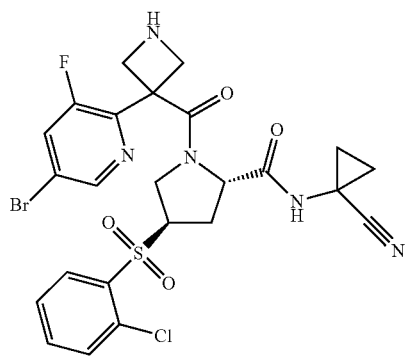 [SMILES: N#CC1(NC(=O)[C@@H]2C[C@@H](S(=O)(=O)c3ccccc3Cl)CN2C(=O)C2(c3ncc(Br)cc3F)CNC2)CC1]

The title compound was prepared in analogy to the methods described for example 2 starting from example 11 to yield a colorless foam. m/z=611.9 [M+H]+.

Example 14

(2S,4R)-1-[3-(5-Bromo-3-fluoro-pyridin-2-yl)-1-methyl-azetidine-3-carbonyl]-4-(2-chloro-benzenesulfonyl)-pyrrolidine-2-carboxylic acid (1-cyano-cyclopropyl)-amide

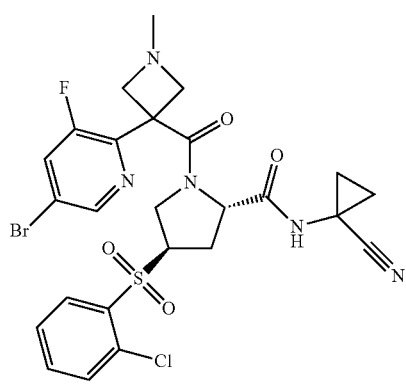 [SMILES: CN1CC(C(=O)N2C[C@H](S(=O)(=O)c3ccccc3Cl)C[C@H]2C(=O)NC2(C#N)CC2)(c2ncc(Br)cc2F)C1]

To a mixture of example 13 (0.05 g, 81.8 µmol, Eq: 1.00), sodium acetate (14.8 mg, 180 µmol, Eq: 2.2) and acetic acid (10.8 mg, 10.3 µl, 180 µmol, Eq: 2.2) in dichloromethane (0.5 ml) was added at 25° C. aqueous formaldehyde solution (36%; 19.1 mg, 17.5 µl, 229 µmol, Eq: 2.8). The mixture was stirred for 45 min, then sodium triacetoxyborohydride (55.5 mg, 262 µmol, Eq: 3.2) was added in one portion at 0-5° C. The cooling bath was removed after 10 min and stirring was continued at 25° C. for further 18 h. The reaction mixture was quenched with aqueous 0.5 M NaOH-solution (2 ml), stirred for 2 min, then the layers were separated. The aqueous layer was extracted with three portions of AcOEt (each 5 ml). The combined organic layers were washed with brine, dried over Na2SO4 and concentrated in vacuo. The crude material was purified by preparative HPLC to yield the title compound as a colorless amorphous solid (0.0206 g; 40%). m/z=626.1 [M+H]+.

Example 15

(2S,4R)-1-[3-(5-Bromo-3-fluoro-pyridin-2-yl)-1-ethyl-azetidine-3-carbonyl]-4-(2-chloro-benzenesulfonyl)-pyrrolidine-2-carboxylic acid (1-cyano-cyclopropyl)-amide

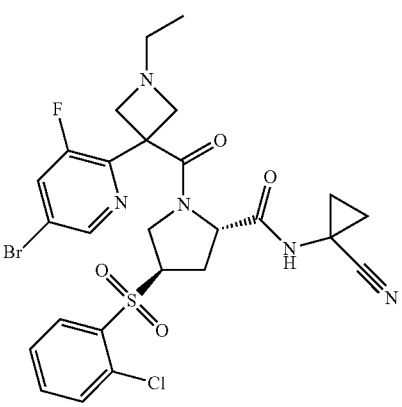 [SMILES: CCN1CC(C(=O)N2C[C@H](S(=O)(=O)c3ccccc3Cl)C[C@H]2C(=O)NC2(C#N)CC2)(c2ncc(Br)cc2F)C1]

The title compound was prepared in analogy to the methods described for example 14 starting from example 13 to yield a light yellow amorphous solid. m/z=640.1 [M+H]+.

Example 16

(2S,4R)-4-(2-Chloro-benzenesulfonyl)-1-[3-(5-chloro-3-fluoro-pyridin-2-yl)-1-methyl-azetidine-3-carbonyl]-pyrrolidine-2-carboxylic acid (1-cyano-cyclopropyl)-amide

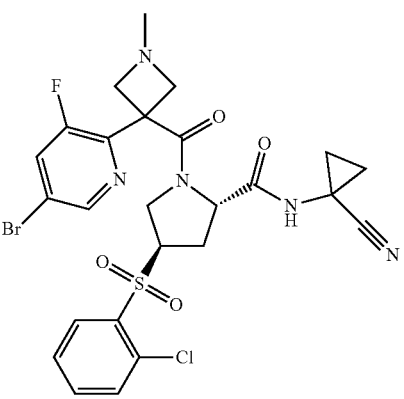 [SMILES: CN1CC(C(=O)N2C[C@H](S(=O)(=O)c3ccccc3Cl)C[C@H]2C(=O)NC2(C#N)CC2)(c2ncc(Br)cc2F)C1]

33

The title compound was prepared in analogy to the methods described for example 14 starting from example 12 to yield a light yellow amorphous solid. m/z=580.1 [M+H]+.

Example 17

3-(5-Chloro-3-fluoro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester

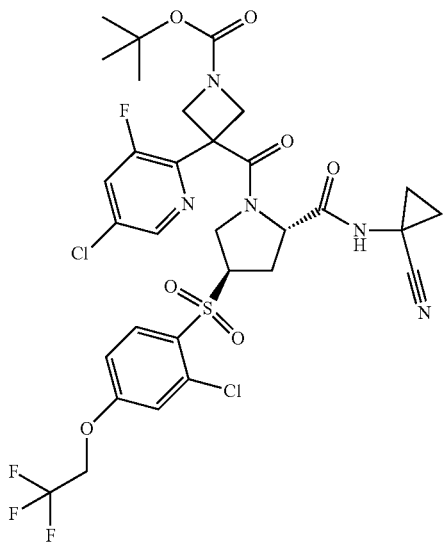 [SMILES: CC(C)(C)OC(=O)N1CC(C(=O)N2C[C@H](S(=O)(=O)c3ccc(OCC(F)(F)F)cc3Cl)C[C@H]2C(=O)NC2(C#N)CC2)(c2ncc(Cl)cc2F)C1]

The title compound was prepared in analogy to the methods described for example 4 to yield a colorless amorphous solid. m/z=764.3 [M+H]+.

Example 18

3-(5-Bromo-3-fluoro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester

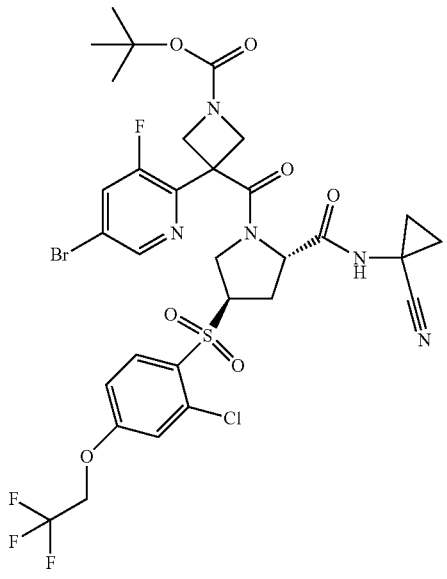 [SMILES: CC(C)(C)OC(=O)N1CC(C(=O)N2C[C@H](S(=O)(=O)c3ccc(OCC(F)(F)F)cc3Cl)C[C@H]2C(=O)NC2(C#N)CC2)(c2ncc(Br)cc2F)C1]

34

The title compound was prepared in analogy to the methods described for example 4 to yield a colorless amorphous solid. m/z=710.1 [M+H−Boc]+.

Example 19

(2S,4R)-1-(3-(5-Bromo-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide

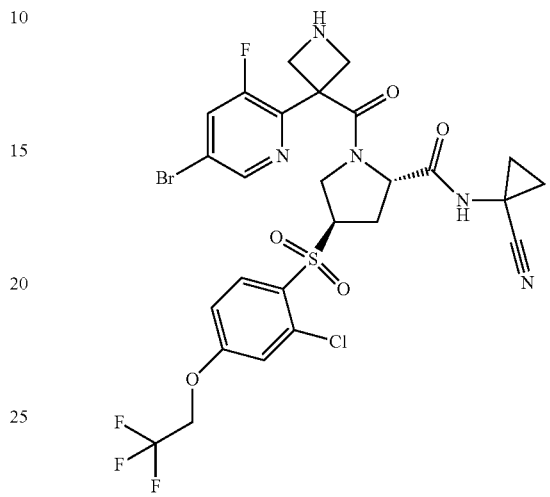

In a 10 mL round-bottomed flask example 18 (0.210 g, 260 µmol, Eq: 1.00) dissolved in dioxane (1.5 ml) and 4 M hydrogen chloride solution in dioxane (260 µl, 1.04 mmol, Eq: 4) were combined to give a colorless solution. The reaction mixture was heated to 22° C. and stirred for 18 h. The crude reaction mixture was concentrated in vacuo and the residue was diluted in AcOEt (30 ml) and extracted with aqueous 10% Na2CO3-solution (50 ml). The aqueous layer was back extracted with AcOEt (2×30 ml). The organic layers were combined, washed with brine (1×20 mL), dried over Na2SO4 and concentrated in vacuo. The crude material was purified by preparative HPLC to yield a colorless amorphous solid (0.038 g; 21%). m/z=710.0 [M+H−Boc]+.

Example 20

(2S,4R)-1-(3-(5-Chloro-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide

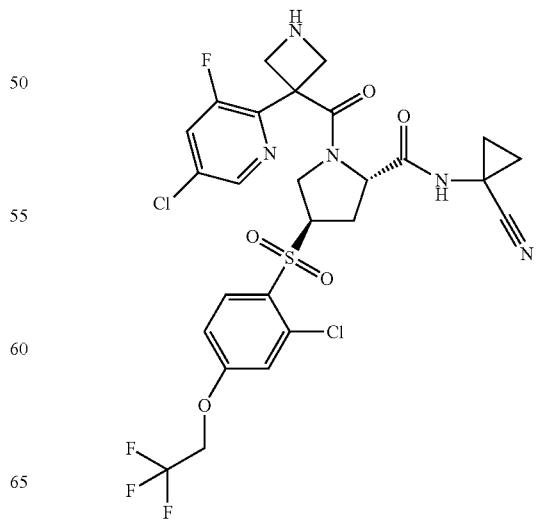

The title compound was prepared in analogy to the methods described for example 19 to yield a colorless amorphous solid. m/z=664.1 [M+H-Boc]⁺.

Example 21

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester

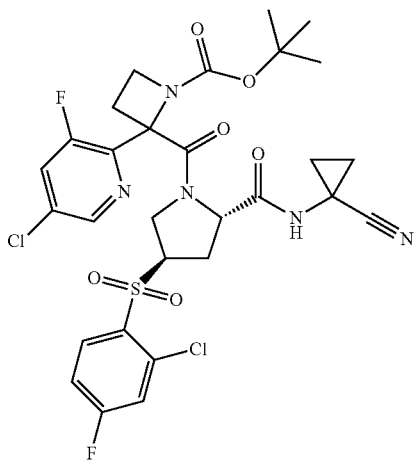 [SMILES: CC(C)(C)OC(=O)N1CCC1(C(=O)N1C[C@H](S(=O)(=O)c2ccc(F)cc2Cl)C[C@H]1C(=O)NC1(C#N)CC1)c1ncc(Cl)cc1F]

A) 2-(5-Chloro-3-fluoro-pyridin-2-yl)-azetidine-1,2-dicarboxylic acid 1-tert-butyl ester 2-methyl ester

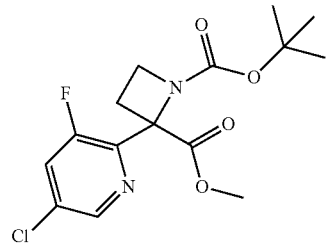 [SMILES: COC(=O)C1(c2ncc(Cl)cc2F)CCN1C(=O)OC(C)(C)C]

To a solution of 5-chloro-2,3-difluoropyridine (1.39 g, 9.29 mmol, Eq: 1.00) and 1-tert-butyl 2-methyl azetidine-1,2-dicarboxylate (2 g, 9.29 mmol, Eq: 1.00) in toluene (15 ml) was added dropwise at 0° C. over 15 min a 0.5 M solution of KHMDS (18.6 ml, 9.29 mmol, Eq: 1.00) in toluene. The colorless solution turned into light brown. After stirring at 0° C. for 45 min, the reaction mixture was allowed to warm up to 25° C. The reaction mixture was stirred for 2.5 h. Saturated aqueous NH₄Cl solution (100 ml) was added and the aqueous phase was extracted with AcOEt (2×150 ml). The combined organic layers were washed with brine, dried over Na₂SO₄, filtered and concentrated under reduced pressure. The crude material was purified by flash chromatography (silica gel, 40 g, 10% to 60% AcOEt in heptane) to yield a colorless viscous oil as a racemate (1.746 g; 55%). m/z=345.2 [M+H]⁺.

B) 2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester [Epimers 1:1]

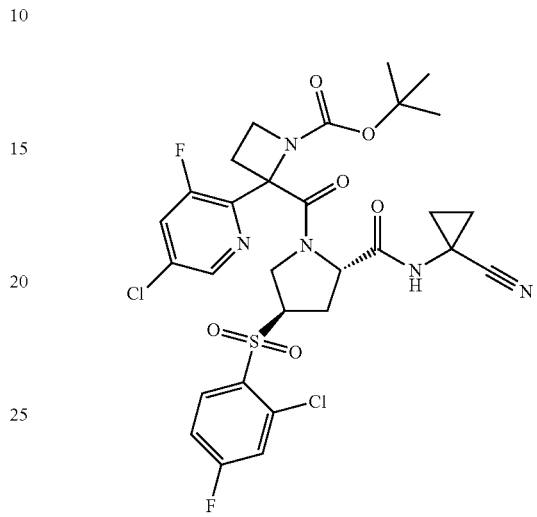

The title compound was prepared in analogy to the methods described for example 1 starting from example 21A) and CAS#1252633-65-0 to yield a mixture of epimers as a colorless amorphous solid. m/z=684.3 [M+H]⁺.

Example 22

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester

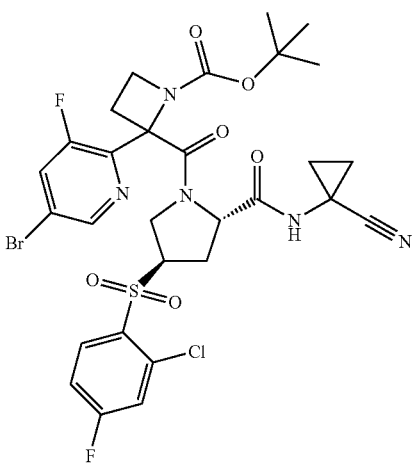 [SMILES: CC(C)(C)OC(=O)N1CCC1(C(=O)N1C[C@H](S(=O)(=O)c2ccc(F)cc2Cl)C[C@H]1C(=O)NC1(C#N)CC1)c1ncc(Cl)cc1F]

The title compound was prepared in analogy to the methods described for example 21. The obtained mixture of epimers was purified by chiral HPLC to yield a single epimer as a colorless amorphous solid. m/z=730.1 [M+H]+.

Example 23

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester

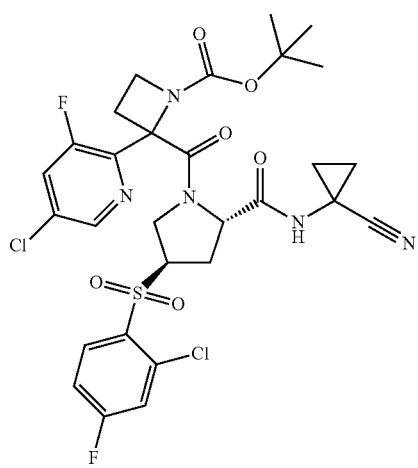 [SMILES: CC(C)(C)OC(=O)N1CCC1(C(=O)N1C[C@H](S(=O)(=O)c2ccc(F)cc2Cl)C[C@H]1C(=O)NC1(C#N)CC1)c1ncc(Cl)cc1F]

Example 23 was obtained as single epimer after chiral HPLC separation of example 21 to yield a single epimer as a colorless amorphous solid. m/z=684.3 [M+H]+.

Example 24

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester

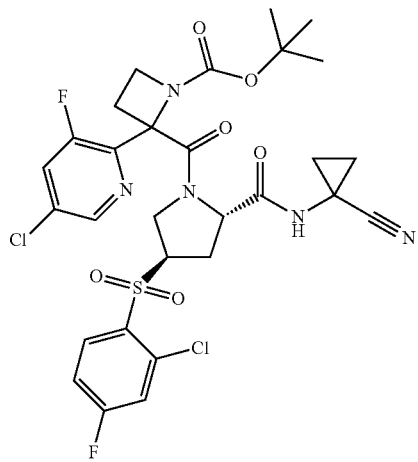 [SMILES: CC(C)(C)OC(=O)N1CCC1(C(=O)N1C[C@H](S(=O)(=O)c2ccc(F)cc2Cl)C[C@H]1C(=O)NC1(C#N)CC1)c1ncc(Cl)cc1F]

Example 24 was obtained as single epimer after chiral HPLC separation of example 21 to yield a single epimer as a colorless amorphous solid. m/z=684.3 [M+H]+.

Example 25

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester

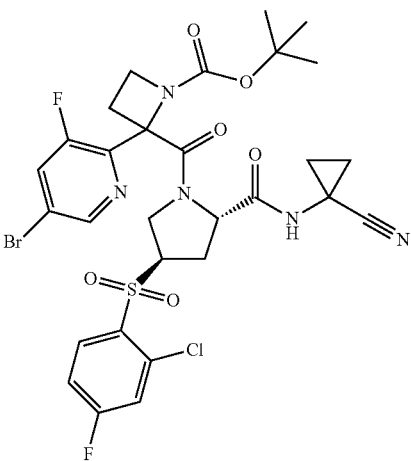

Example 25 was obtained as single epimer after chiral HPLC separation of example 22 to yield a single epimer as a colorless amorphous solid. m/z=730.1 [M+H]+.

Example 26

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester

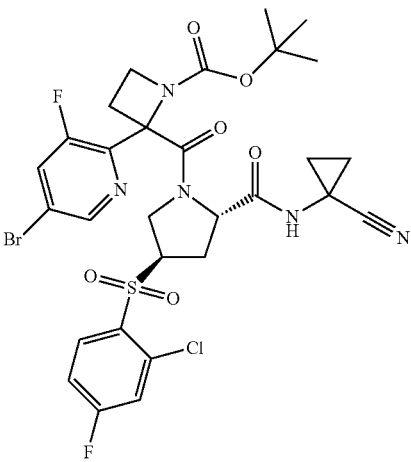

Example 26 was obtained as single epimer after chiral HPLC separation of example 22 to yield a single epimer as a colorless amorphous solid. m/z=730.1 [M+H]⁺.

Example 27 tert-butyl 2-(5-chloro-3-fluoropyridin-2-yl)-2-((2S, 4R)-4-(2-chloro-4-((S)-1,1,1-trifluoropropan-2-yloxy)phenylsulfonyl)-2-(1-cyanocyclopropylcarbamoyl)pyrrolidine-1-carbonyl)azetidine-1-carboxylate

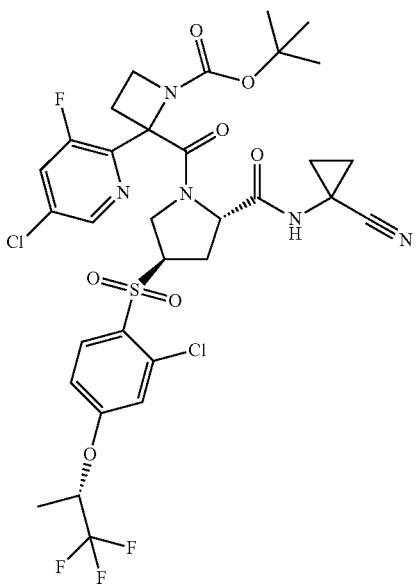 [SMILES: C[C@H](Oc1ccc(S(=O)(=O)[C@@H]2C[C@@H](C(=O)NC3(C#N)CC3)N(C(=O)C3(c4ncc(Cl)cc4F)CCN3C(=O)OC(C)(C)C)C2)c(Cl)c1)C(F)(F)F]

In a 25 ml round-bottomed flask example 21 (0.1 g, 146 µmol, Eq: 1.00) was combined with N,N-dimethylacetamide (1.5 ml) to give a light yellow solution. (S)-1,1,1-trifluoropropan-2-ol (26.7 mg, 234 µmol, Eq: 1.6) and cesium carbonate (57.1 mg, 175 µmol, Eq: 1.2) were added at 25° C. to above solution and stirred for 24 h. After that, additional (S)-1,1,1-trifluoropropan-2-ol (6.67 mg, 58.4 µmol, Eq: 0.4) was added to the reaction mixture and stirred for further 24 h at 25° C. The crude reaction mixture was concentrated, the residue was dissolved in AcOEt (100 ml), extracted in succession with aqueous 0.5 N HCl-solution (35 ml) and aqueous 10% Na₂CO₃-solution (25 ml). The aqueous layer was back extracted with AcOEt (2×25 ml). The combined organic layers were washed with brine, dried over Na₂SO₄, filtered and evaporated. The crude material was subsequently purified by flash chromatography (silica gel, 40 g, 10% to 50% EtOAc in heptane) to yield a mixture of epimers which was then subsequently purified with chiral HPLC to yield one epimer as an amorphous colorless solid (9 mg; 8%). m/z=778.3 [M+H]⁺

Example 28 tert-butyl 2-(5-chloro-3-fluoropyridin-2-yl)-2-((2S, 4R)-4-(2-chloro-4-((S)-1,1,1-trifluoropropan-2-yloxy)phenylsulfonyl)-2-(1-cyanocyclopropylcarbamoyl)pyrrolidine-1-carbonyl)azetidine-1-carboxylate

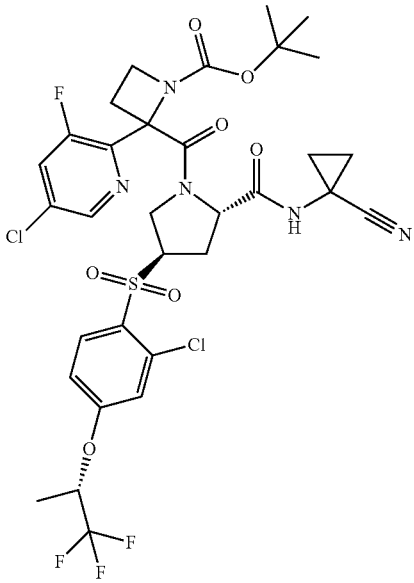 [SMILES: C[C@H](Oc1ccc(S(=O)(=O)[C@@H]2C[C@@H](C(=O)NC3(C#N)CC3)N(C(=O)C3(c4ncc(Cl)cc4F)CCN3C(=O)OC(C)(C)C)C2)c(Cl)c1)C(F)(F)F]

Example 28 was obtained after chiral HPLC purification of example 27 as the other epimer. m/z=778.3 [M+H]⁺.

Example 29

2-(5-Bromo-3-fluoro-pyridin-2-yl)-2-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester

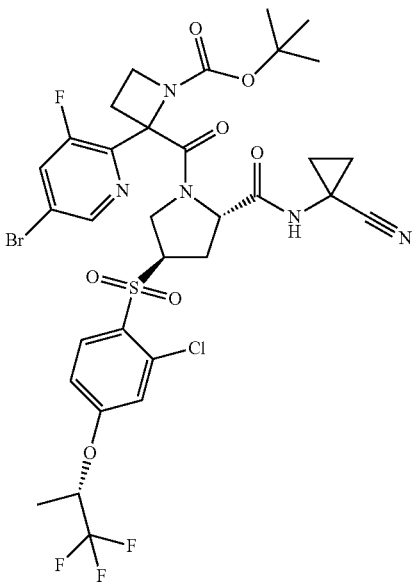

The title compound was prepared in analogy to the methods described for example 27. The obtained mixture of epimers was purified by chiral HPLC to yield a single epimer as a colorless amorphous solid. m/z=842.1 [M+H]+.

Example 30

2-(5-Bromo-3-fluoro-pyridin-2-yl)-2-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester

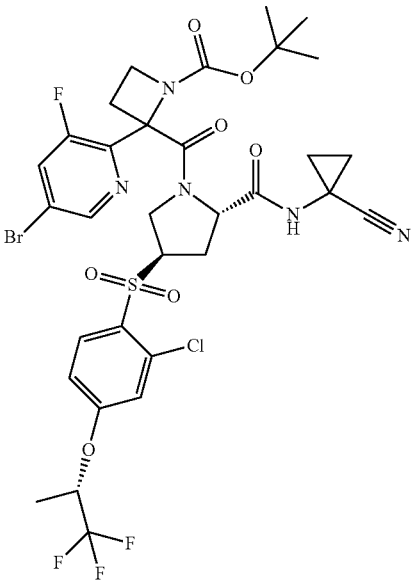

Example 30 was obtained after chiral HPLC purification of example 27 as the other epimer. m/z=842.1 [M+H]+.

Example 31

(2S,4R)-4-(2-Chloro-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide; hydrochloride

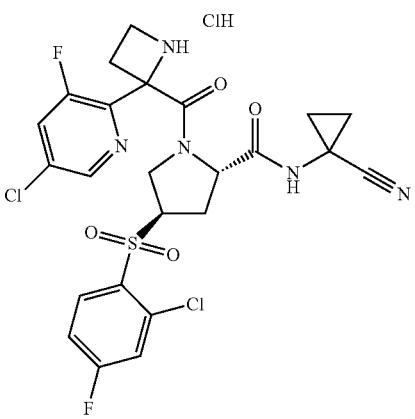 [SMILES: Cl ; N#CC1(NC(=O)[C@@H]2C[C@@H](S(=O)(=O)c3ccc(F)cc3Cl)CN2C(=O)C2(c3ncc(Cl)cc3F)CCN2)CC1]

In a 10 mL round-bottomed flask example 24 (0.034 g, 49.7 μmol, Eq: 1.00) in dioxane (0.1 ml) and 4 M hydrogen chloride solution in dioxane (62.1 μl, 248 μmol, Eq: 5) were combined to give a colorless solution. The reaction mixture was heated to 22° C. and stirred for 18 h. After that, 4 M hydrogen chloride solution in dioxane (62.1 μl, 248 μmol, Eq: 5) was added and the reaction mixture was stirred for 24 h at 25° C. After that, additional 4 M hydrogen chloride solution in dioxane (24.8 μl, 99.3 μmol, Eq: 2) was added and the mixture was stirred for 2 h. The reaction mixture was concentrated in vacuo to yield an off-white foam (0.031 g; 100%). m/z=584.0 [M+H]+.

Example 32

(2S,4R)-4-(2-Bromo-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide hydrochloride

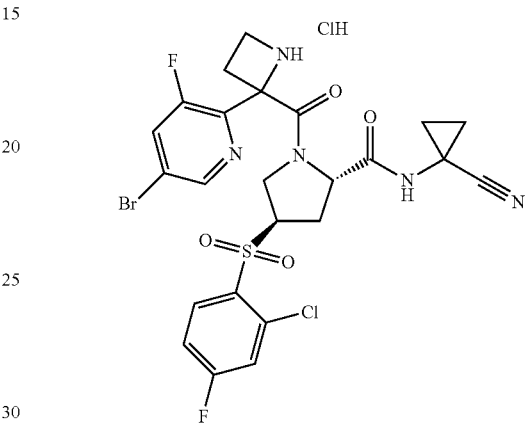

The title compound was prepared from example 26 in analogy to example 31 to yield an off-white solid. m/z=630.2 [M+H]+.

Example 33

3-(5-Bromo-3-fluoro-pyridin-2-yl)-3-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester

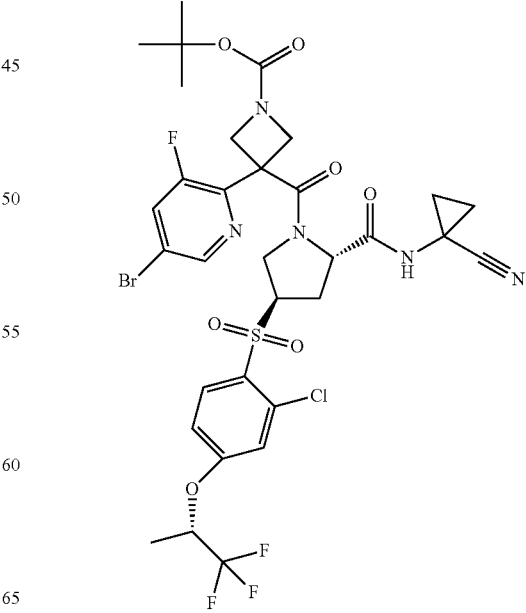

The title compound was prepared in analogy to the methods described for examples 1 and 11 starting from CAS #1252636-85-3 to yield a colorless waxy solid. m/z=824.1 [M+H]$^+$.

Example 34

(2S,4R)-1-[3-(5-Bromo-3-fluoro-pyridin-2-yl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide

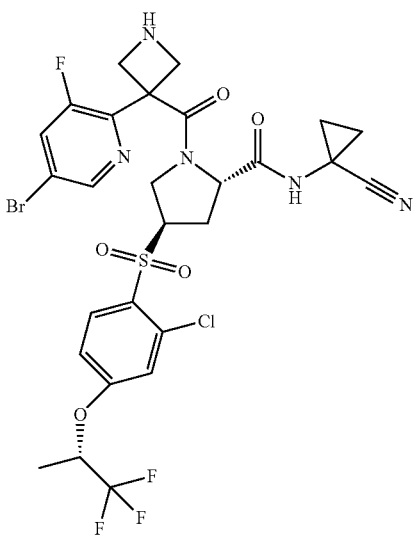 [SMILES: C[C@H](Oc1ccc(S(=O)(=O)[C@@H]2C[C@@H](C(=O)NC3(C#N)CC3)N(C(=O)C3(c4ncc(Br)cc4F)CNC3)C2)c(Cl)c1)C(F)(F)F]

The title compound was prepared from example 33 using the methods described for example 31. After evaporation the compound was purified with preparative HPLC to yield a white solid. m/z=724.2 [M+H]$^+$.

Example 35

(2S,4R)-4-(2-Chloro-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide hydrochloride

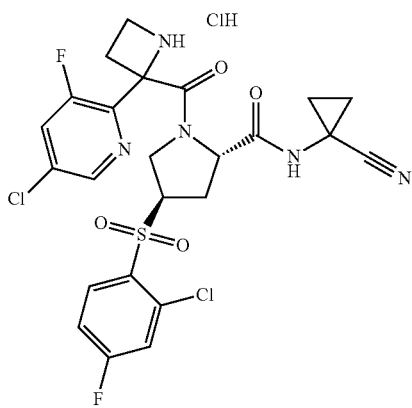 [SMILES: N#CC1(NC(=O)[C@@H]2C[C@@H](S(=O)(=O)c3ccc(F)cc3Cl)CN2C(=O)C2(c3ncc(Cl)cc3F)CCN2)CC1 ; Cl]

The title compound was prepared from example 23 using the methods described for example 31 to yield a colorless solid. m/z=584.2 [M+H]$^+$.

Example 36

(2S,4R)-1-[2-(5-Bromo-3-fluoro-pyridin-2-yl)-azetidine-2-carbonyl]-4-(2-chloro-4-fluoro-benzenesulfonyl)-pyrrolidine-2-carboxylic acid (1-cyano-cyclopropyl)-amide hydrochloride

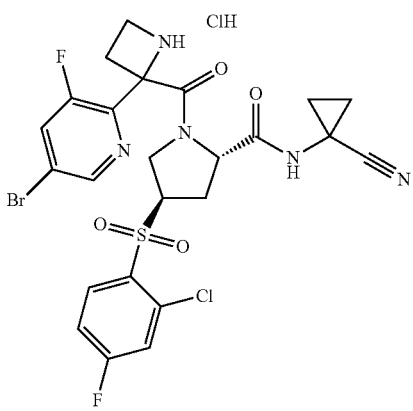 [SMILES: N#CC1(NC(=O)[C@@H]2C[C@@H](S(=O)(=O)c3ccc(F)cc3Cl)CN2C(=O)C2(c3ncc(Br)cc3F)CCN2)CC1 ; Cl]

The title compound was prepared from example 25 using the methods described for example 31 to yield a colorless solid. m/z=630.2 [M+H]$^+$.

Example 37

(2S,4R)-1-[2-(5-Chloro-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide hydrochloride

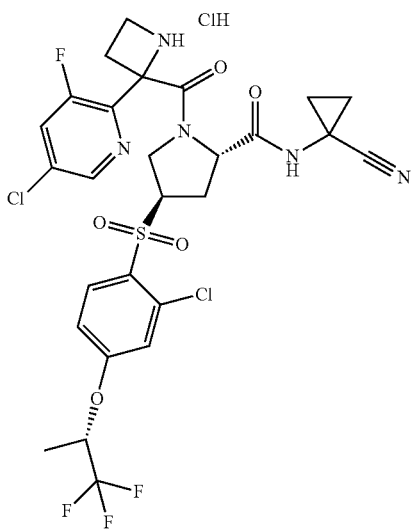 [SMILES: C[C@H](Oc1ccc(S(=O)(=O)[C@@H]2C[C@@H](C(=O)NC3(C#N)CC3)N(C(=O)C3(c4ncc(Cl)cc4F)CCN3)C2)c(Cl)c1)C(F)(F)F ; Cl]

The title compound was prepared from example 27 using the methods described for example 31 to yield a colorless solid. m/z=678.2 [M+H]+.

Example 38

(2S,4R)-1-[2-(5-Chloro-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide hydrochloride

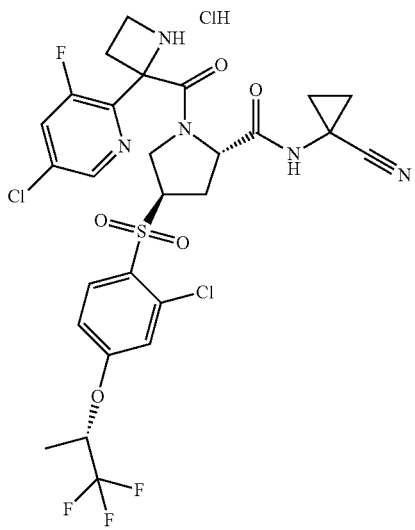 [SMILES: C[C@H](Oc1ccc(S(=O)(=O)[C@@H]2C[C@@H](C(=O)NC3(C#N)CC3)N(C(=O)C3(c4ncc(Cl)cc4F)CCN3)C2)c(Cl)c1)C(F)(F)F ; Cl]

The title compound was prepared from example 28 using the methods described for example 31 to yield a colorless solid. m/z=678.2 [M+H]+.

Example 39

(2S,4R)-1-[2-(5-Bromo-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide hydrochloride

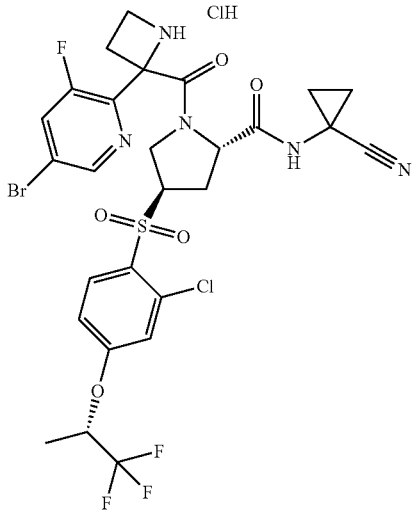 [SMILES: C[C@H](Oc1ccc(S(=O)(=O)[C@@H]2C[C@@H](C(=O)NC3(C#N)CC3)N(C(=O)C3(c4ncc(Br)cc4F)CCN3)C2)c(Cl)c1)C(F)(F)F ; Cl]

The title compound was prepared from example 29 using the methods described for example 31 to yield a colorless solid. m/z=724.1 [M+H]+.

Example 40

(2S,4R)-1-[3-(5-Bromo-3-fluoro-pyridin-2-yl)-1-methyl-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide

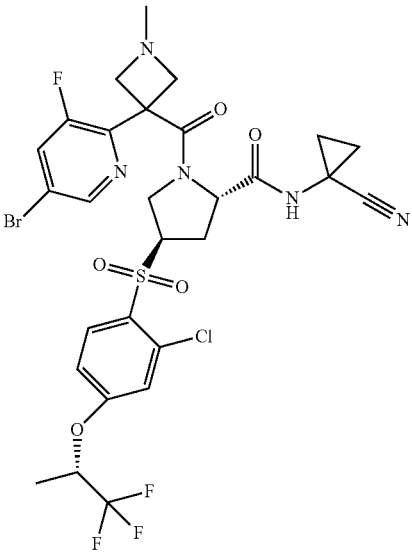 [SMILES: C[C@H](Oc1ccc(S(=O)(=O)[C@@H]2C[C@@H](C(=O)NC3(C#N)CC3)N(C(=O)C3(c4ncc(Br)cc4F)CN(C)C3)C2)c(Cl)c1)C(F)(F)F]

The title compound was prepared from example 34 according to the methods described for example 14 to yield an amorphous colorless solid. m/z=756.3 [M+H]+.

Example 41

2-(5-Chloro-3-fluoro-pyridin-2-yl)-2-[(2S,4R)-4-[2-chloro-4-(2-methyl-pyridin-4-yl)-benzenesulfonyl]-2-(1-cyano-cyclopropylcarbamoyl)-pyrrolidine-1-carbonyl]-azetidine-1-carboxylic acid tert-butyl ester

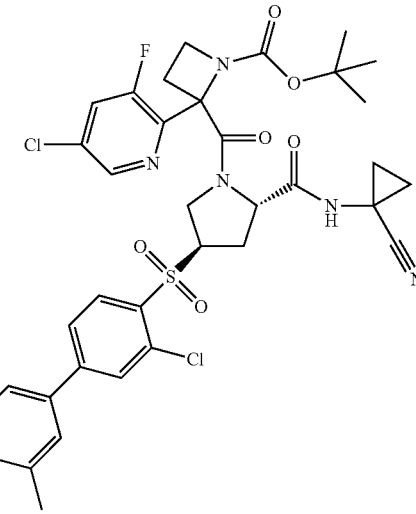

A) (2S,4R)-4-(4-Bromo-2-chloro-phenylsulfanyl)-pyrrolidine-1,2-dicarboxylic acid 1-tert-butyl ester 2-methyl ester

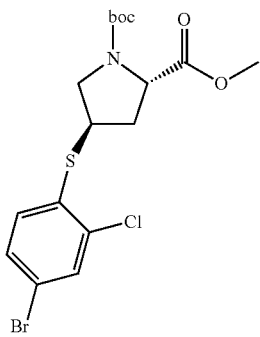

CAS #1252633-25-2 (5.3 g, 12.3 mmol, Eq: 1.00) was dissolved in propionitrile (40 ml) and 4-bromo-2-chlorobenzenethiol (3.3 g, 14.8 mmol, Eq: 1.20) was added. Now triethyl amine (2.49 g, 3.43 ml, 24.6 mmol, Eq: 2.00) was added. The reaction mixture was stirred at reflux over night. The reaction mixture was poured into 100 ml 10% $Na_2CO_3$ and extracted with EtOAc (2×100 mL). The organic layer was extracted with 100 ml 0.1N HCl, dried over $Na_2SO_4$, filtered and evaporated. The crude material was purified by flash chromatography (silica gel, 120 g, 0% to 30% AcOEt in heptane in 30 min) to yield a colorless oil (4.72 g; 85%). m/z=352.1 [M+H-Boc]$^+$.

B) (2S,4R)-4-(4-Bromo-2-chloro-benzenesulfonyl)-pyrrolidine-1,2-dicarboxylic acid 1-tert-butyl ester 2-methyl ester

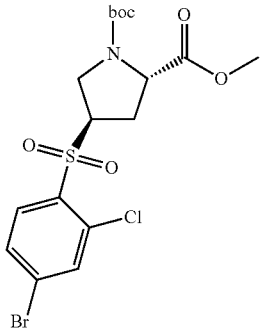

Example 41A (4.72 g, 10.5 mmol, Eq: 1.00) was dissolved in dichloromethane (40 ml) and MCPBA (3.79 g, 22.0 mmol, Eq: 2.10) was carefully portion-wise added. The reaction mixture was stirred for 18 h at 25° C. The reaction mixture was extracted with aqueous 10% $Na_2CO_3$ solution, aqueous 0.1 N HCl solution and saturated aqueous $Na_2S_2O_3$ solution. The organic layers were dried over $Na_2SO_4$ and $Na_2SO_3$ for 2 h, filtered and carefully evaporated to yield a colorless waxy solid (4.96 g; 98%). m/z=383.9 [M+H-Boc]+$^+$.

C) (2S,4R)-4-(4-Bromo-2-chloro-benzenesulfonyl)-pyrrolidine-1,2-dicarboxylic acid 1-tert-butyl ester

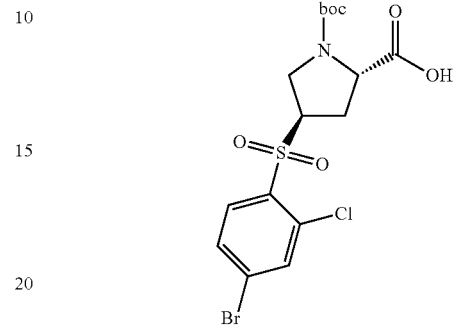

Example 41B (4.96 g, 10.3 mmol, Eq: 1.00) was dissolved in THF (15 ml) and water (10 ml). Now LiOH hydrate (418 mg, 17.5 mmol, Eq: 1.70) was added and the reaction mixture was stirred 3 h at 22° C. The reaction mixture was extracted with aqueous 0.2 N HCl solution/dichloromethane. The organic layers were dried over $Na_2SO_4$, filtered and concentrated in vacuo to a white foam (4.83 g; 100%). m/z=467.9 [M-H]$^-$.

D) (2S,4R)-4-(4-Bromo-2-chloro-benzenesulfonyl)-2-(1-cyano-cyclopropylcarbamoyl)-pyrrolidine-1-carboxylic acid tert-butyl ester

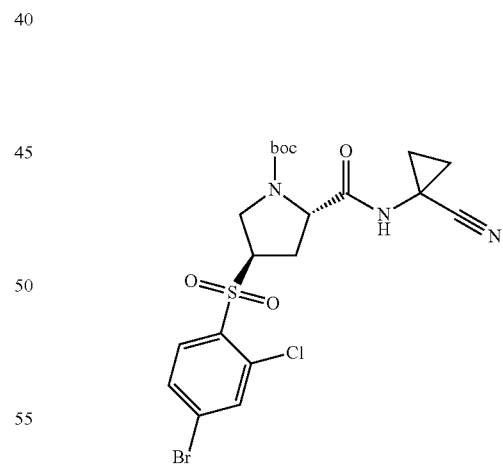

Example 41C (4.83 g, 10.3 mmol, Eq: 1.00) was dissolved in acetonitrile (40 ml). HATU (7.84 g, 20.6 mmol, Eq: 2.00), DIEA (2.66 g, 3.6 ml, 20.6 mmol, Eq: 2.00) and 1-aminocyclopropane-carbonitrile hydrochloride (1.47 g, 12.4 mmol, Eq: 1.20) were added to the solution and stirred at 22° C. for 2 h. The reaction mixture was poured into aqueous 0.1 M HCl (100 ml) and extracted with dischloromethane (3×75 mL). The organic layers were dried over Na$_2$SO$_4$ and concentrated in vacuo. The crude material was purified by flash chromatography (silica gel, 120 g, 0% to 60% AcOEt in heptane) to yield a white solid (3.2 g; 58%). m/z=531.9 [M−H]$^-$.

E) (2S,4R)-4-(4-Bromo-2-chloro-benzenesulfonyl)-pyrrolidine-2-carboxylic acid (1-cyano-cyclopropyl)-amide

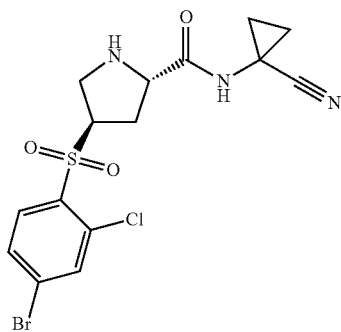 [SMILES: N#CC1(NC(=O)[C@@H]2C[C@@H](S(=O)(=O)c3ccc(Br)cc3Cl)CN2)CC1]

The title compound was prepared according to the methods described for example 2 to yield an off-white solid. m/z=434.1 [M+H]$^+$.

F) 2-[(2S,4R)-4-(4-Bromo-2-chloro-benzenesulfonyl)-2-(1-cyano-cyclopropylcarbamoyl)-pyrrolidine-1-carbonyl]-2-(4-chloro-2-fluoro-phenyl)-azetidine-1-carboxylic acid tert-butyl ester

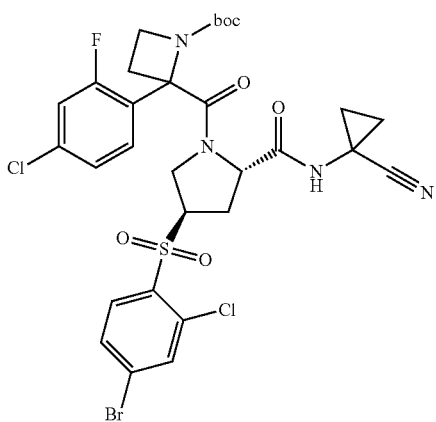

The title compound was prepared in analogy to the methods described for example 21 to yield a colorless foam. m/z=746.0 [M+H]$^+$.

G) 2-(5-Chloro-3-fluoro-pyridin-2-yl)-2-[(2S,4R)-4-[2-chloro-4-(2-methyl-pyridin-4-yl)-benzenesulfonyl]-2-(1-cyano-cyclopropylcarbamoyl)-pyrrolidine-1-carbonyl]-azetidine-1-carboxylic acid tert-butyl ester

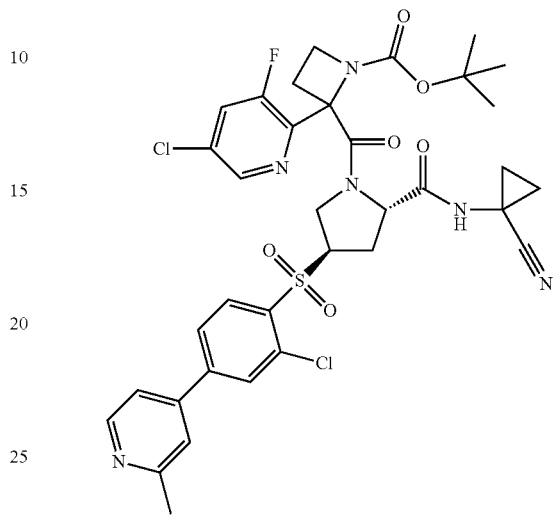

To a 10 ml microwave vial was added example 41G) (0.05 g, 67.1 μmol, Eq: 1.00), 2-methylpyridine-4-boronic acid pinacol ester (16.2 mg, 73.8 μmol, Eq: 1.1) and tripotassium phosphate (42.7 mg, 201 μmol, Eq: 3) and 2'-(dimethylamino)-2-biphenyl-palladium (II) chloridedinorbomlphosphine complex (3.76 mg, 6.71 μmol, Eq: 0.1) in water (1.0 ml) and dioxane (2.5 ml). The vial was capped and heated in the microwave at 120° C. for 30 min. The crude material was purified by preparative HPLC to yield a colorless foam (0.019 g; 37%). m/z=757.4 [M+H]$^+$.

Example 42

2-(5-Bromo-3-fluoro-pyridin-2-yl)-2-[(2S,4R)-4-[2-chloro-4-(2-methyl-pyridin-4-yl)-benzenesulfonyl]-2-(1-cyano-cyclopropylcarbamoyl)-pyrrolidine-1-carbonyl]-azetidine-1-carboxylic acid tert-butyl ester

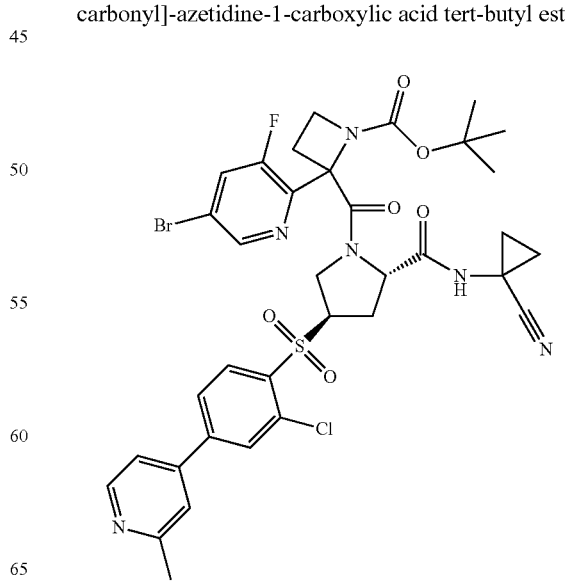

Example 43

(2S,4R)-1-[2-(5-Chloro-3-fluoro-pyridin-2-yl)-azetidine-2-carbonyl]-4-[2-chloro-4-(2-methyl-pyridin-4-yl)-benzenesulfonyl]-pyrrolidine-2-carboxylic acid (1-cyano-cyclopropyl)-amide hydrochloride

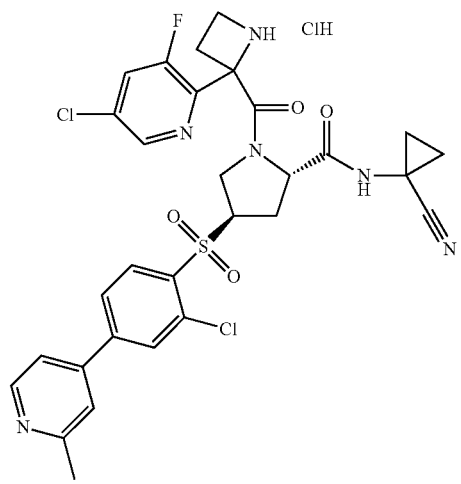 [SMILES: Cc1cc(-c2ccc(S(=O)(=O)[C@@H]3C[C@@H](C(=O)NC4(C#N)CC4)N(C(=O)C4(c5ncc(Cl)cc5F)CCN4)C3)c(Cl)c2)ccn1 ; Cl]

The title compound was prepared from example 41 in analogy to example 31 to yield a white solid. m/z=657.4 [M+H]⁺.

Example 44

(2S,4R)-1-[2-(5-Bromo-3-fluoro-pyridin-2-yl)-azetidine-2-carbonyl]-4-[2-chloro-4-(2-methyl-pyridin-4-yl)-benzenesulfonyl]-pyrrolidine-2-carboxylic acid (1-cyano-cyclopropyl)-amide hydrochloride

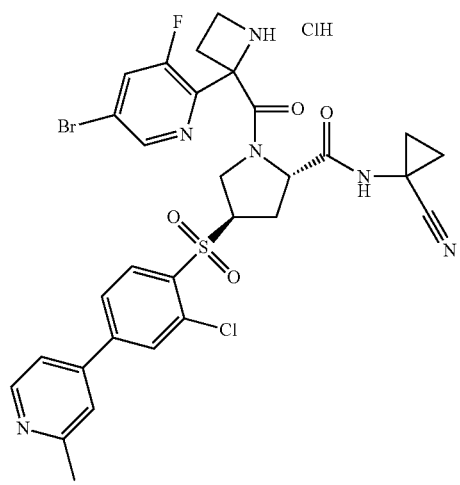 [SMILES: Cc1cc(-c2ccc(S(=O)(=O)[C@@H]3C[C@@H](C(=O)NC4(C#N)CC4)N(C(=O)C4(c5ncc(Br)cc5F)CCN4)C3)c(Cl)c2)ccn1 ; Cl]

The title compound was prepared in analogy to the methods described for example 21 and 41 to yield a colorless amorphous solid. m/z=803.1 [M+H]⁺.

The title compound was prepared from example 42 in analogy to example 31 to yield a white amorphous solid. m/z=703.3 [M+H]⁺.

Example 45 tert-butyl 2-(5-chloro-3-fluoropyridin-2-yl)-2-((2S,4R)-4-(2-chloro-4-(1-methyl-1H-pyrazol-4-yl)phenylsulfonyl)-2-(1-cyanocyclopropylcarbamoyl)pyrrolidine-1-carbonyl)azetidine-1-carboxylate

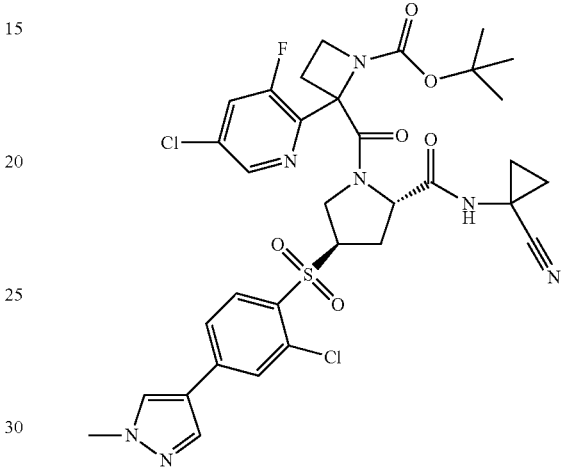

The title compound was prepared from example 41F) and 1-methyl-4-(4,4,5,5-tetramethyl-1,3,2-dioxaborolan-2-yl)-1H-pyrazole in analogy to the method of example 41G) to yield a colorless foam. m/z=746.3 [M+H]⁺.

Example 46 tert-butyl 2-(5-bromo-3-fluoropyridin-2-yl)-2-((2S,4R)-4-(2-chloro-4-(1-methyl-1H-pyrazol-4-yl)phenylsulfonyl)-2-(1-cyanocyclopropylcarbamoyl)pyrrolidine-1-carbonyl)azetidine-1-carboxylate

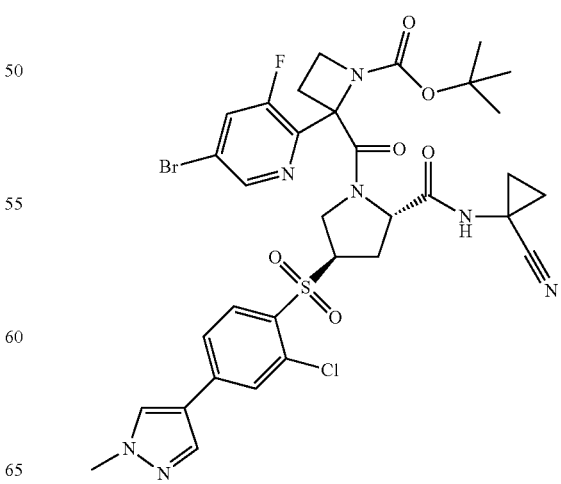

Example 47

(2S,4R)-1-[2-(5-Chloro-3-fluoro-pyridin-2-yl)-azetidine-2-carbonyl]-4-[2-chloro-4-(1-methyl-1H-pyrazol-4-yl)-benzenesulfonyl]-pyrrolidine-2-carboxylic acid (1-cyano-cyclopropyl)-amide hydrochloride

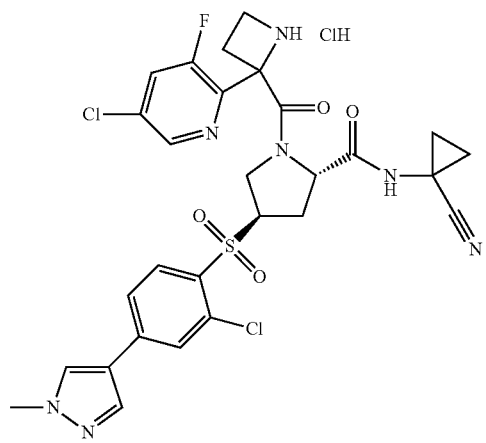 [SMILES: Cn1cc(-c2ccc(S(=O)(=O)[C@@H]3C[C@@H](C(=O)NC4(C#N)CC4)N(C(=O)C4(c5ncc(Cl)cc5F)CCN4)C3)c(Cl)c2)cn1 ; Cl]

The title compound was prepared from example 45 in analogy to example 31 to yield a white solid. m/z=646.5 [M+H]$^+$.

Example 48

(2S,4R)-1-[2-(5-Bromo-3-fluoro-pyridin-2-yl)-azetidine-2-carbonyl]-4-[2-chloro-4-(1-methyl-1H-pyrazol-4-yl)-benzenesulfonyl]-pyrrolidine-2-carboxylic acid (1-cyano-cyclopropyl)-amide hydrochloride

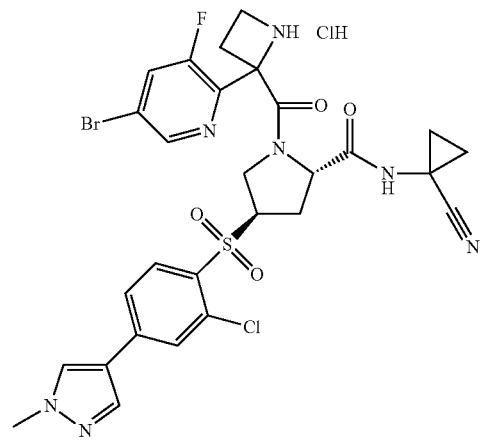 [SMILES: Cn1cc(-c2ccc(S(=O)(=O)[C@@H]3C[C@@H](C(=O)NC4(C#N)CC4)N(C(=O)C4(c5ncc(Br)cc5F)CCN4)C3)c(Cl)c2)cn1 ; Cl]

The title compound was prepared in analogy to example 42 and 45 to yield a colorless foam. m/z=746.3 [M+H]$^+$.

The title compound was prepared from example 46 in analogy to example 31 to yield a colorless foam. m/z=692.2 [M+H]$^+$.

Example 49

(2S,4R)-1-[3-(5-Bromo-3-fluoro-pyridin-2-yl)-1-(2,2-difluoro-ethyl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide

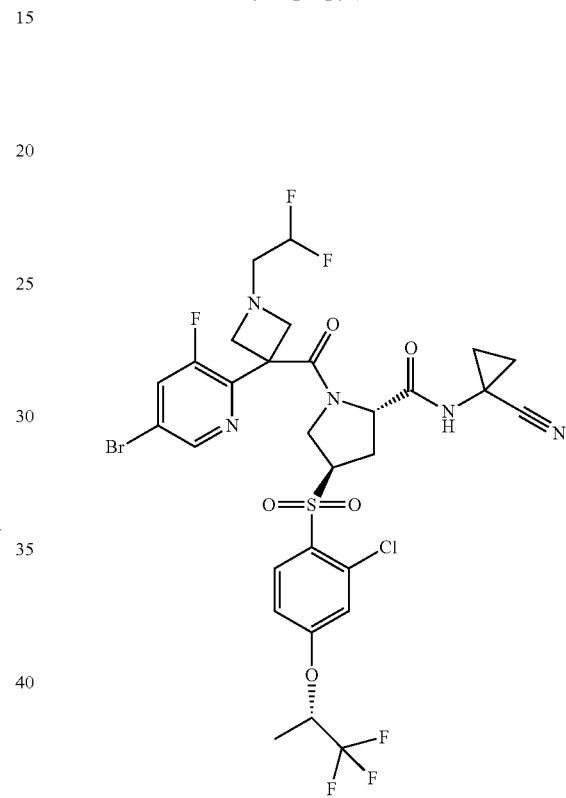

In a 5 ml round-bottomed flask, example 34 (100 mg, 138 μmol, Eq: 1.00), 2,2-difluoroethyl trifluoromethanesulfonate (51.8 mg, 34.3 μl, 242 μmol, Eq: 1.75) and Hunig's base (31.3 mg, 42.3 μl, 242 μmol, Eq: 1.75) were combined with Acetonitrile (1.5 ml) to give a light yellow solution. The reaction mixture was stirred for 4 h at 25° C. The crude reaction mixture was concentrated in vacuo. The reaction mixture was poured into EtOAc (20 ml) and extracted with aqueous 10% Na$_2$CO$_3$ solution (1×15 mL). The aqueous layer was back-extracted with EtOAc (2×20 mL). The organic layers were combined, washed with saturated aqueous NaCl solution (1×15 mL). The organic layers were dried over Na$_2$SO$_4$ and concentrated in vacuo. The crude material was purified by flash chromatography (silica gel, 12 g, 10% to 80% EtOAc in heptane) to yield the title compound as a colorless amorphous solid (41 mg; 38%). m/z=786.0415 [M–H]$^-$.

Example 50

(2S,4R)-1-[3-(5-Bromo-3-fluoro-pyridin-2-yl)-1-formyl-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide

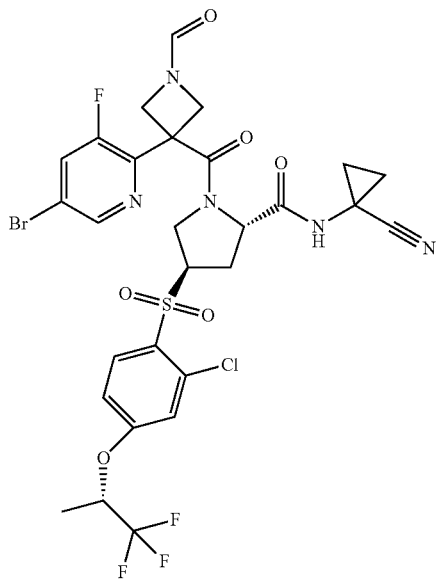 [SMILES: C[C@H](Oc1ccc(S(=O)(=O)[C@@H]2C[C@@H](C(=O)NC3(C#N)CC3)N(C(=O)C3(c4ncc(Br)cc4F)CN(C=O)C3)C2)c(Cl)c1)C(F)(F)F]

In a 5 ml round-bottomed flask, example 34 was combined with DMSO (0.5 ml) to give a colorless solution. 4-Nitrophenyl formate (12.7 mg, 76.1 µmol, Eq: 1.10) was added. The reaction mixture was stirred for 3 days at 25° C. After that, additional 4-nitrophenyl formate (3.47 mg, 20.7 µmol, Eq: 0.3) were added to above solution and stirred for 5 days. The crude material was purified by preparative HPLC to yield the title compound as a colorless amorphous solid (14 mg; 27%). m/z=752.0394 [M+H]$^+$.

Example 51

3-(5-Bromo-3-fluoro-pyridin-2-yl)-3-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid methyl ester

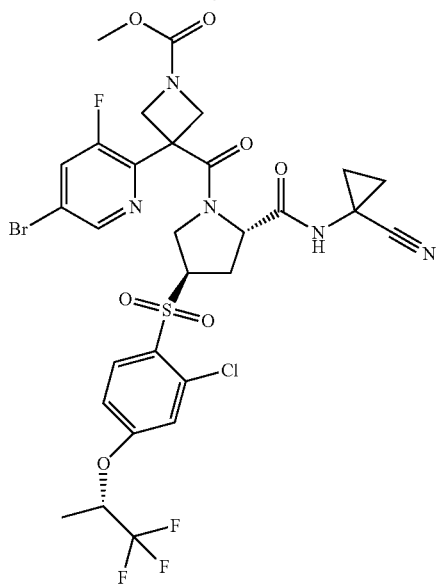 [SMILES: COC(=O)N1CC(C(=O)N2C[C@H](S(=O)(=O)c3ccc(O[C@@H](C)C(F)(F)F)cc3Cl)C[C@H]2C(=O)NC2(C#N)CC2)(c2ncc(Br)cc2F)C1]

In a 5 ml round-bottomed flask, example 34 (50 mg, 69.2 µmol, Eq: 1.00) was combined with dichloromethane (1.0 ml) to give a colorless solution. Methyl chloroformate (13.1 mg, 10.7 µl, 138 µmol, Eq: 2.00) and triethylamine (14.0 mg, 19.3 µl, 138 µmol, Eq: 2.00) were added. The reaction mixture stirred for 4 h at 25° C. The crude material was purified by preparative HPLC to yield the title compound as a white solid (15 mg; 27%). m/z=782.0487 [M+H]$^+$.

Example 52

(2S,4R)-1-[3-(5-Bromo-3-fluoro-pyridin-2-yl)-1-(2,2,2-trifluoro-ethyl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide

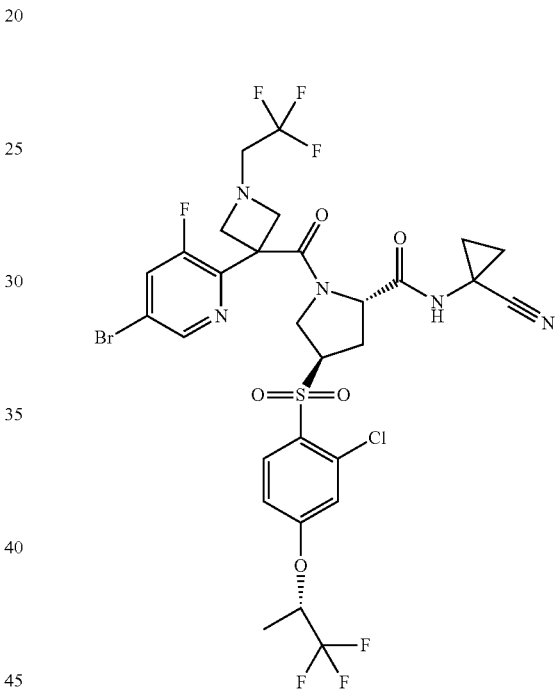

In a 5 ml round-bottomed flask, example 34 (50 mg, 69.2 µmol, Eq: 1.00) was combined with acetonitrile (1.5 ml) to give a colorless solution. 2,2,2-Trifluoroethyl trifluoromethanesulfonate (20.1 mg, 12.5 µL, 86.5 µmol, Eq: 1.25) and Hunig's base (11.2 mg, 15.1 µL, 86.5 µmol, Eq: 1.25) were added. The reaction mixture stirred for 18 h at 25° C. The crude material was purified by preparative HPLC to yield the title compound as a colorless solid (12 mg; 22%). m/z=806.0479 [M+H]$^+$.

Example 53

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DTT 5 mM.

Enzymes (all at 1 nM): human and mouse Cathepsin S, Cat K, Cat B, Cat L.

Substrate (20 μM): Z-Val-Val-Arg-AMC, except for Cat K which uses Z-Leu-Arg-AMC (both from Bachem).

Z=Benzyloxycarbonyl.
AMC=7-Amino-4-Methyl-Coumarin.
DTT=dithiothreitol.
Final volume: 100 μL.
Excitation 360 nm, Emission 465 nm.

Enzyme is added to the substance dilutions in 96-well microtitre plates and the reaction is started with substrate. Fluorescence emission is measured over 20 minutes, during which time a linear increase is observed in the absence of inhibitor. $IC_{50}$ are calculated by standard methods.

Inhibition of human Cat S, mouse Cat S, human Cat K, human Cat B, human Cat L and mouse Cat L have been measured separately. The results obtained for human Cat S and L for representative compounds of the invention are expressed in the following table in μM.

| Example | IC50 h L | IC50 h S |
|---|---|---|
| 1 | 1.073 | 0.003223 |
| 2 | 0.0381 | 0.001486 |
| 3 | 0.2923 | 0.001198 |
| 4 | 1.239 | 0.002749 |
| 5 | 0.7531 | 0.003687 |
| 6 | 0.0898 | 0.003158 |
| 7 | 0.0735 | 0.003823 |
| 8 | 0.1413 | 0.000694 |
| 9 | 0.0917 | 0.000779 |
| 10 | 0.1939 | 0.00126 |
| 11 | 0.0705 | 0.001269 |
| 12 | 0.0236 | 0.001066 |
| 13 | 0.0046 | 0.001086 |
| 14 | 0.0125 | 0.000613 |
| 15 | 0.0201 | 0.000721 |
| 16 | 0.0398 | 0.000525 |
| 17 | | |
| 18 | | |
| 19 | 0.0338 | 0.001666 |
| 20 | 0.0782 | 0.002917 |
| 21 | 1.338 | 0.001045 |
| 22 | 1.016 | 0.001257 |
| 23 | 2.013 | 0.000377 |
| 24 | 0.922 | 0.00456 |
| 25 | 2.909 | 0.000492 |
| 26 | 0.4708 | 0.004445 |
| 27 | 0.5277 | 0.007062 |
| 28 | 0.5565 | 0.001078 |
| 29 | 0.1883 | 0.005501 |
| 30 | 1.057 | 0.002219 |
| 31 | 0.0816 | 0.001574 |
| 32 | 0.0485 | 0.001769 |
| 33 | 0.0895 | 0.003542 |
| 34 | 0.0142 | 0.003478 |
| 35 | 1.435 | 0.001299 |
| 36 | 0.621 | 0.001424 |
| 37 | 0.0585 | 0.003826 |
| 38 | 0.3172 | 0.004161 |
| 39 | 0.0269 | 0.005455 |
| 40 | 0.0166 | 0.002134 |
| 41 | 0.523 | 0.001553 |
| 42 | 0.6616 | 0.004597 |
| 43 | 0.0866 | 0.00233 |
| 44 | 0.0706 | 0.002076 |
| 45 | 0.6251 | 0.000965 |
| 46 | 1.163 | 0.001124 |
| 47 | 0.0821 | 0.000791 |
| 48 | 0.0989 | 0.001854 |
| 49 | 0.005 | 0.001 |
| 50 | 0.005 | 0.0009 |

-continued

| Example | IC50 h L | IC50 h S |
|---|---|---|
| 51 | 0.007 | 0.002 |
| 52 | 0.006 | 0.001 |

The compounds of the invention are preferential inhibitors of Cathepsin-S and L over Cathepsin-K and B.

The compounds according to the invention have, in the foregoing assay, an $IC_{50}$ at Cat S and/or L which is between 0.00001 and 100 μM, preferably between 0.00001 and 50 μM, more preferably between 0.00001 and 20 μM. The particular compounds of the invention have an $IC_{50}$ in at least one of the foregoing assay below 0.09 μM.

Example A

A compound of formula (I) can be used in a manner known per se as the active ingredient for the production of tablets of the following composition:
Per Tablet

| | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:
Per Capsule

| | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:
1. A compound of formula (I)

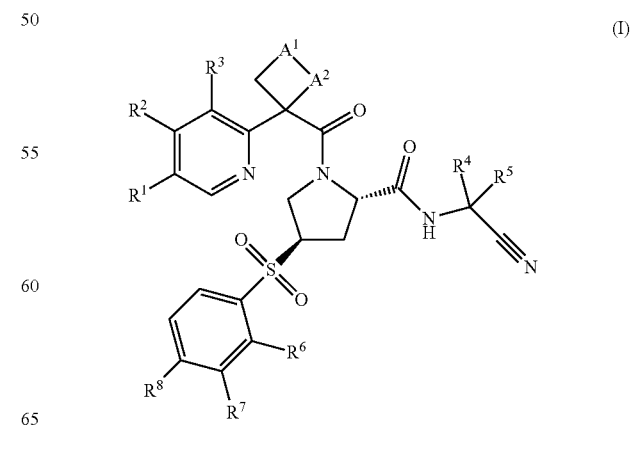

wherein
one of $A^1$ and $A^2$ is —$NR^9$— and the other one is —$CH_2$—;
$R^1$ is halogen;
$R^2$ is hydrogen, halogen, alkyl or haloalkyl;
$R^3$ is hydrogen, halogen, alkyl or haloalkyl;
$R^4$ and $R^5$ are both hydrogen at the same time;
or $R^4$ and $R^5$ together with the carbon atom to which they are attached form cycloalkyl;
$R^6$ is hydrogen, halogen, alkyl, haloalkyl or cycloalkyl;
$R^7$ is hydrogen, halogen, alkyl, haloalkyl or cycloalkyl;
$R^8$ is hydrogen, alkyl, haloalkyl, alkoxy, haloalkoxy, cycloalkyl, alkylpyrdinyl, alkyl-1H-pyrazolyl, phenyl, substituted phenyl, heterocyclyl or substituted heterocyclyl, wherein heterocyclyl is pyridinyl, pyrimidinyl, pyrazinyl, pyridazinyl, pyrrolyl, pyrazolyl, imidazolyl, triazolyl, oxazolyl, isoxazolyl, oxadiazolyl, thiophenyl, thiazolyl, thiadiazolyl, piperidinyl, piperazinyl, pyrrolidinyl or morpholinyl, wherein substituted phenyl is phenyl substituted with one to three substituents independently selected from alkyl, halogen, cycloalkyl, haloalkyl, alkoxy, haloalkoxy, halocycloalkyl and nitrile and wherein substituted heterocyclyl is heterocyclyl substituted with one to three substituents independently selected from alkyl, halogen, cycloalkyl, haloalkyl, alkoxy, haloalkoxy, halocycloalkyl and nitrile; and
$R^9$ is hydrogen, alkyl, haloalkyl, cycloalkyl, acyl or alkoxycarbonyl;
or a pharmaceutically acceptable salt thereof.

2. A compound according to claim 1, wherein $R^1$ is chloro or bromo.

3. A compound according to claim 1, wherein $R^2$ is hydrogen.

4. A compound according to claim 1, wherein $R^3$ is hydrogen or halogen.

5. A compound according to claim 1, wherein $R^3$ is hydrogen or fluoro.

6. A compound according to claim 1, wherein $R^4$ and $R^5$ together with the carbon atom to which they are attached form cyclopropyl.

7. A compound according to claim 1, wherein $R^6$ is halogen.

8. A compound according to claim 1, wherein $R^6$ is chloro.

9. A compound according to claim 1, wherein $R^7$ is hydrogen.

10. A compound according to claim 1, wherein $R^8$ is hydrogen, halogen, alkoxy, haloalkoxy, cycloalkyl, alkylpyridinyl or alkyl-1H-pyrazolyl.

11. A compound according to claim 1, wherein $R^8$ is hydrogen, halogen, alkoxy, haloalkoxy, alkylpyridinyl or alkyl-1H-pyrazolyl.

12. A compound according to claim 1, wherein $R^8$ is hydrogen, fluoro, methoxy, trifluoroethoxy, trifluoropropoxy, methylpyridinyl or methyl-1H-pyrazolyl.

13. A compound according to claim 1, wherein $R^9$ is hydrogen, alkyl, haloalkyl, formyl or alkoxycarbonyl.

14. A compound according to claim 1, wherein $R^9$ is hydrogen, methyl, ethyl, difluoroethyl, formyl, methoxycarbonyl or trifluoroethyl.

15. A compound according to claim 1 selected from:
3-[(2S,4R)-4-(2-Chloro-4-methoxy-benzenesulfonyl)-2-(1-cyano-cyclopropylcarbamoyl)-pyrrolidine-1-carbonyl]-3-(5-chloro-pyridin-2-yl)-azetidine-1-carboxylic acid tert-butyl ester;
(2S,4R)-4-(2-Chloro-4-methoxy-benzenesulfonyl)-1-[3-(5-chloro-pyridin-2-yl)-azetidine-3-carbonyl]-pyrrolidine-2-carboxylic acid (1-cyano-cyclopropyl)-amide;
(2S,4R)-4-(2-Chloro-4-methoxy-benzenesulfonyl)-1-[3-(5-chloro-pyridin-2-yl)-1-methyl-azetidine-3-carbonyl]-pyrrolidine-2-carboxylic acid (1-cyano-cyclopropyl)-amide;
3-(5-Chloro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester;
3-(5-Bromo-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester;
(2S,4R)-1-[3-(5-Chloro-pyridin-2-yl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide;
(2S,4R)-1-[3-(5-Bromo-pyridin-2-yl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide;
(2S,4R)-1-[3-(5-Chloro-pyridin-2-yl)-1-(2,2-difluoro-ethyl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide;
(2S,4R)-1-[3-(5-Bromo-pyridin-2-yl)-1-(2,2-difluoro-ethyl)-azetidine-3-carbonyl]-4-[2-chloro-4-(2,2,2-trifluoro-ethoxy)-benzenesulfonyl]-pyrrolidine-2-carboxylic acid (1-cyano-cyclopropyl)-amide;
3-[(2S,4R)-4-(2-Chloro-benzenesulfonyl)-2-(1-cyano-cyclopropylcarbamoyl)-pyrrolidine-1-carbonyl]-3-(5-chloro-3-fluoro-pyridin-2-yl)-azetidine-1-carboxylic acid tert-butyl ester;
tert-Butyl 3-(5-bromo-3-fluoropyridin-2-yl)-3-((2S,4R)-4-(2-chlorophenylsulfonyl)-2-(1-cyanocyclopropylcarbamoyl)pyrrolidine-1-carbonyl)azetidine-1-carboxylate;
(2S,4R)-1-(3-(5-Chloro-3-fluoropyridin-2-yl)azetidine-3-carbonyl)-4-(2-chlorophenylsulfonyl)-N-(1-cyanocyclopropyl)pyrrolidine-2-carboxamide;
(2S,4R)-1-[3-(5-Bromo-3-fluoro-pyridin-2-yl)-azetidine-3-carbonyl]-4-(2-chloro-benzenesulfonyl)-pyrrolidine-2-carboxylic acid (1-cyano-cyclopropyl)-amide;
(2S,4R)-1-[3-(5-Bromo-3-fluoro-pyridin-2-yl)-1-methyl-azetidine-3-carbonyl]-4-(2-chloro-benzenesulfonyl)-pyrrolidine-2-carboxylic acid (1-cyano-cyclopropyl)-amide;
(2S,4R)-1-[3-(5-Bromo-3-fluoro-pyridin-2-yl)-1-ethyl-azetidine-3-carbonyl]-4-(2-chloro-benzenesulfonyl)-pyrrolidine-2-carboxylic acid (1-cyano-cyclopropyl)-amide;
(2S,4R)-4-(2-Chloro-benzenesulfonyl)-1-[3-(5-chloro-3-fluoro-pyridin-2-yl)-1-methyl-azetidine-3-carbonyl]-pyrrolidine-2-carboxylic acid (1-cyano-cyclopropyl)-amide;
3-(5-Chloro-3-fluoro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester;
3-(5-Bromo-3-fluoro-pyridin-2-yl)-3-[(2S,4R)-4-[2-chloro-4-(2,2,2-trifluoro-ethoxy)-benzenesulfonyl]-2-(1-cyano-cyclopropylcarbamoyl)-pyrrolidine-1-carbonyl]-azetidine-1-carboxylic acid tert-butyl ester;
(2S,4R)-1-(3-(5-Bromo-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide;

(2S,4R)-1-(3-(5-Chloro-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide;

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester;

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester;

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester;

2-[(2S,4R)-4-(2-Chloro-4-fluoro-benzenesulfonyl)-2-(1-cyano-cyclopropylcarbamoyl)-pyrrolidine-1-carbonyl]-2-(5-chloro-3-fluoro-pyridin-2-yl)-azetidine-1-carboxylic acid tert-butyl ester;

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester;

2-(5-Bromo-3-fluoro-pyridin-2-yl)-2-[(2S,4R)-4-(2-chloro-4-fluoro-benzenesulfonyl)-2-(1-cyano-cyclopropylcarbamoyl)-pyrrolidine-1-carbonyl]-azetidine-1-carboxylic acid tert-butyl ester;

tert-Butyl 2-(5-chloro-3-fluoropyridin-2-yl)-2-((2S,4R)-4-(2-chloro-4-((S)-1,1,1-trifluoropropan-2-yloxy)phenylsulfonyl)-2-(1-cyanocyclopropylcarbamoyl)pyrrolidine-1-carbonyl)azetidine-1-carboxylate;

tert-Butyl 2-(5-chloro-3-fluoropyridin-2-yl)-2-((2S,4R)-4-(2-chloro-4-((S)-1,1,1-trifluoropropan-2-yloxy)phenylsulfonyl)-2-(1-cyanocyclopropylcarbamoyl)pyrrolidine-1-carbonyl)azetidine-1-carboxylate;

2-(5-Bromo-3-fluoro-pyridin-2-yl)-2-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester;

2-(5-Bromo-3-fluoro-pyridin-2-yl)-2-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester;

(2S,4R)-4-(2-Chloro-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide;

(2S,4R)-4-(2-Bromo-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide;

3-(5-Bromo-3-fluoro-pyridin-2-yl)-3-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid tert-butyl ester;

(2S,4R)-1-[3-(5-Bromo-3-fluoro-pyridin-2-yl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-4-(2-Chloro-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-(2-chloro-4-fluoro-benzenesulfonyl)-pyrrolidine-2-carboxylic acid (1-cyano-cyclopropyl)-amide;

(2S,4R)-1-[2-(5-Chloro-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Chloro-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-methyl-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

2-(5-Chloro-3-fluoro-pyridin-2-yl)-2-[(2S,4R)-4-[2-chloro-4-(2-methyl-pyridin-4-yl)-benzenesulfonyl]-2-(1-cyano-cyclopropylcarbamoyl)-pyrrolidine-1-carbonyl]-azetidine-1-carboxylic acid tert-butyl ester;

2-(5-Bromo-3-fluoro-pyridin-2-yl)-2-[(2S,4R)-4-[2-chloro-4-(2-methyl-pyridin-4-yl)-benzenesulfonyl]-2-(1-cyano-cyclopropylcarbamoyl)-pyrrolidine-1-carbonyl]-azetidine-1-carboxylic acid tert-butyl ester;

(2S,4R)-1-[2-(5-Chloro-3-fluoro-pyridin-2-yl)-azetidine-2-carbonyl]-4-[2-chloro-4-(2-methyl-pyridin-4-yl)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-(2-methyl-pyridin-4-yl)-benzenesulfonyl]-pyrrolidine-2-carboxylic acid (1-cyano-cyclopropyl)-amide;

tert-Butyl 2-(5-chloro-3-fluoropyridin-2-yl)-2-((2S,4R)-4-(2-chloro-4-(1-methyl-1H-pyrazol-4-yl)phenylsulfonyl)-2-(1-cyanocyclopropylcarbamoyl)pyrrolidine-1-carbonyl)azetidine-1-carboxylate;

tert-Butyl 2-(5-bromo-3-fluoropyridin-2-yl)-2-((2S,4R)-4-(2-chloro-4-(1-methyl-1H-pyrazol-4-yl)phenylsulfonyl)-2-(1-cyanocyclopropylcarbamoyl)pyrrolidine-1-carbonyl)azetidine-1-carboxylate;

(2S,4R)-1-[2-(5-Chloro-3-fluoro-pyridin-2-yl)-azetidine-2-carbonyl]-4-[2-chloro-4-(1-methyl-1H-pyrazol-4-yl)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-(1-methyl-1H-pyrazol-4-yl)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-(2,2-difluoro-ethyl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-formyl-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

3-(5-Bromo-3-fluoro-pyridin-2-yl)-3-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid methyl ester; and (2S,4R)-1-[3-(5-Bromo-3-fluoro-pyridin-2-yl)-1-(2,2,2-trifluoro-ethyl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide.

16. A compound according to any one of claim 1 selected from (2S,4R)-4-(2-Chloro-4-methoxy-benzenesulfonyl)-1-[3-(5-chloro-pyridin-2-yl)-azetidine-3-carbonyl]-pyrrolidine-2-carboxylic acid (1-cyano-cyclopropyl)-amide;

(2S,4R)-1-(3-(5-chloro-3-fluoropyridin-2-yl)azetidine-3-carbonyl)-4-(2-chlorophenylsulfonyl)-N-(1-cyanocyclopropyl)pyrrolidine-2-carboxamide;

(2S,4R)-1-[3-(5-Bromo-3-fluoro-pyridin-2-yl)-azetidine-3-carbonyl]-4-(2-chloro-benzenesulfonyl)-pyrrolidine-2-carboxylic acid (1-cyano-cyclopropyl)-amide;

(2S,4R)-1-[3-(5-Bromo-3-fluoro-pyridin-2-yl)-1-methyl-azetidine-3-carbonyl]-4-(2-chloro-benzenesulfonyl)-pyrrolidine-2-carboxylic acid (1-cyano-cyclopropyl)-amide;

(2S,4R)-1-[3-(5-Bromo-3-fluoro-pyridin-2-yl)-1-ethyl-azetidine-3-carbonyl]-4-(2-chloro-benzenesulfonyl)-pyrrolidine-2-carboxylic acid (1-cyano-cyclopropyl)-amide;

(2S,4R)-4-(2-Chloro-benzenesulfonyl)-1-[3-(5-chloro-3-fluoro-pyridin-2-yl)-1-methyl-azetidine-3-carbonyl]-pyrrolidine-2-carboxylic acid (1-cyano-cyclopropyl)-amide;

(2S,4R)-1-(3-(5-Bromo-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide;

(2S,4R)-1-(3-(5-Chloro-3-fluoropyridin-2-yl)azetidine-3-carbonyl)-4-(2-chloro-4-(2,2,2-trifluoroethoxy)phenylsulfonyl)-N-(1-cyanocyclopropyl)pyrrolidine-2-carboxamide;

(2S,4R)-4-(2-Bromo-4-fluoro-benzenesulfonyl)-1-[2-(5-chloro-3-fluoro-pyridin-2-yl)-azetidine-2-carbonyl]-pyrrolidine-2-carboxylic acid (1-cyano-cyclopropyl)-amide;

(2S,4R)-1-[3-(5-Bromo-3-fluoro-pyridin-2-yl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Chloro-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-methyl-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[2-(5-Bromo-3-fluoro-pyridin-2-yl)-azetidine-2-carbonyl]-4-[2-chloro-4-(2-methyl-pyridin-4-yl)-benzenesulfonyl]-pyrrolidine-2-carboxylic acid (1-cyano-cyclopropyl)-amide;

(2S,4R)-1-[2-(5-Chloro-3-fluoro-pyridin-2-yl)-azetidine-2-carbonyl]-4-[2-chloro-4-(1-methyl-1H-pyrazol-4-yl)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-(2,2-difluoro-ethyl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[3-(5-Bromo-3-fluoro-pyridin-2-yl)-1-formyl-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

3-(5-Bromo-3-fluoro-pyridin-2-yl)-3-[(2S,4R)-4-[2-chloro-4-((S)-2,2,2-trifluoro-1-methyl-ethoxy)-benzenesulfonyl]-2-(1-cyano-cyclopropylcarbamoyl)-pyrrolidine-1-carbonyl]-azetidine-1-carboxylic acid methyl ester; and (2S,4R)-1-[3-(5-Bromo-3-fluoro-pyridin-2-yl)-1-(2,2,2-trifluoro-ethyl)-azetidine-3-carbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide.

17. A process for the preparation of a compound of formula (I) according to claim 1 comprising one of the following steps:

(a) The reaction of a compound of formula (II)

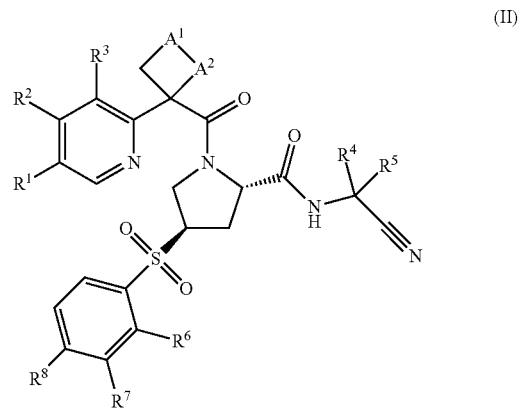

(II)

in the presence of acid, wherein $R^1$ to $R^8$ are as defined in any one of claims 1 to 14, one of $A^1$ and $A^2$ is —CH$_2$— and the other one is —NR$^{10}$— wherein $R^{10}$ is an amine protecting group;

(b) The reaction of a compound of formula (III)

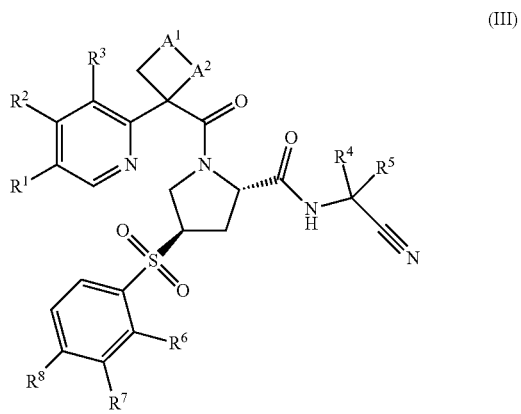

(III)

in the presence of $R^9$—X, wherein $A^1$, $A^2$ and $R^1$ to $R^9$ are as defined in any one of claims 1 to 14; or (c) The reaction of a compound of formula (III) as defined above in the presence of $R^{10}$—C(O)—Y and a reducing agent, wherein $A^1$, $A^2$ and $R^1$ to $R^9$ are as defined in any one of claims 1 to 14, $R^{10}$ is alkyl, haloalkyl or cycloalkyl and Y is hydrogen, alkyl or haloalkyl.

18. A pharmaceutical composition comprising a compound in accordance with claim 1 and a therapeutically inert carrier.

* * * * *

UNITED STATES PATENT AND TRADEMARK OFFICE
CERTIFICATE OF CORRECTION

PATENT NO. : 8,822,505 B2
APPLICATION NO. : 13/760519
DATED : September 2, 2014
INVENTOR(S) : Lilli Anselm et al.

Page 1 of 1

It is certified that error appears in the above-identified patent and that said Letters Patent is hereby corrected as shown below:

On the title page item 73 Assignee: Genentech, Inc., South San Francisco, CA (US)

Please delete "Genentech, Inc., South San Francisco, CA (US)" and insert -- Hoffmann-La Roche Inc., Little Falls, NJ --

Signed and Sealed this
Twenty-second Day of March, 2016

Michelle K. Lee
*Director of the United States Patent and Trademark Office*